US012569210B2

(12) United States Patent　　(10) Patent No.:　US 12,569,210 B2
Jenkins et al.　　(45) Date of Patent:　　Mar. 10, 2026

(54) COREGISTRATION RELIABILITY WITH EXTRALUMINAL IMAGE AND INTRALUMINAL DATA

(71) Applicant: PHILIPS IMAGE GUIDED THERAPY CORPORATION, San Diego, CA (US)

(72) Inventors: Rebecca Ann Jenkins, San Diego, CA (US); Emily Winkler Brown, Amsterdam (NL); Ryan Michael Sotak, Colorado Springs, CO (US); Ehud Nachtomy, Herzliya (IL); Ronald Christiaan Helmstrijd, Best (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 170 days.

(21) Appl. No.: 18/290,103

(22) PCT Filed: May 5, 2022

(86) PCT No.: PCT/EP2022/062141
　§ 371 (c)(1),
　(2) Date: Nov. 9, 2023

(87) PCT Pub. No.: WO2022/238229
　PCT Pub. Date: Nov. 17, 2022

(65) Prior Publication Data
　US 2024/0245374 A1　　Jul. 25, 2024
Related U.S. Application Data

(60) Provisional application No. 63/187,962, filed on May 13, 2021.

(51) Int. Cl.
　*A61B 6/00*　　　(2024.01)
　*A61B 8/00*　　　(2006.01)
　　　　(Continued)

(52) U.S. Cl.
　CPC ............ *A61B 6/487* (2013.01); *A61B 6/5247* (2013.01); *A61B 8/0891* (2013.01); *A61B 8/12* (2013.01);
　　　　(Continued)

(58) Field of Classification Search
　CPC ....... A61B 6/4441; A61B 6/481; A61B 6/487; A61B 6/5247; A61B 8/0841; A61B 8/085;
　　　　(Continued)

(56) References Cited

U.S. PATENT DOCUMENTS

| | | |
|---|---|---|
| 6,776,763 B2 | 8/2004 | Nix |
| 7,226,417 B1 | 6/2007 | Eberle |

(Continued)

FOREIGN PATENT DOCUMENTS

| | | |
|---|---|---|
| WO | 2022161790 A1 | 8/2022 |
| WO | 2022238058 A1 | 11/2022 |

(Continued)

OTHER PUBLICATIONS

International Search Report and Written Opinion of PCT/EP2022/062141, dated Jul. 21, 2022.

(Continued)

*Primary Examiner* — Dani Fox

(57)　　　　ABSTRACT

A co-registration system includes a processor circuit that generates and displays a first co-registration reliability indicator based on the status of an x-ray imaging device and a second co-registration reliability indicator based on the speed of an intravascular catheter/guidewire. The processor circuit receives, from the x-ray imaging device, x-ray images of a blood vessel while the intravascular catheter/guidewire moves through the blood vessel. The processor circuit receives, from the catheter/guidewire, intravascular data representative of the blood vessel while the catheter/

(Continued)

guidewire moves through the blood vessel. The processor circuit co-registers the intravascular data to an x-ray image received from the x-ray imaging device. The processor circuit also receives a signal representative of an inactive status of the x-ray imaging device during the movement of the catheter/guidewire. The processor circuit then displays the first reliability indicator representative of the x-ray fluoroscopy device status and may indicate that co-registration is not possible. The processor circuit also determines a speed of the catheter/guidewire and displays a second indicator representative of the speed of the catheter/guidewire being too fast for reliable co-registration.

20 Claims, 10 Drawing Sheets

(51) Int. Cl.
   *A61B 8/08*        (2006.01)
   *A61B 8/12*        (2006.01)

(52) U.S. Cl.
   CPC ............ *A61B 8/4416* (2013.01); *A61B 8/463* (2013.01); *A61B 8/5261* (2013.01)

(58) Field of Classification Search
   CPC ....... A61B 8/0883; A61B 8/0891; A61B 8/12; A61B 8/4245; A61B 8/4416; A61B 8/463; A61B 8/5207; A61B 8/5261
   See application file for complete search history.

(56) References Cited

U.S. PATENT DOCUMENTS

| | | | |
|---|---|---|---|
| 7,846,101 | B2 | 12/2010 | Eberle |
| 7,930,014 | B2 | 4/2011 | Huennekens |
| 8,290,228 | B2 | 10/2012 | Cohen |
| 8,463,007 | B2 | 6/2013 | Steinberg |
| 8,670,603 | B2 | 3/2014 | Tolkowsky |
| 8,693,756 | B2 | 4/2014 | Tolkowsky |
| 8,781,193 | B2 | 7/2014 | Steinberg |
| 8,855,744 | B2 | 10/2014 | Tolkowsky |
| 10,076,301 | B2 | 9/2018 | Millett |
| 2006/0241465 | A1* | 10/2006 | Huennekens ............ A61B 5/06 600/458 |
| 2015/0305710 | A1 | 10/2015 | Stigall |
| 2017/0065206 | A1 | 3/2017 | Bozkaya |
| 2020/0069264 | A1 | 3/2020 | Merritt |
| 2020/0129142 | A1 | 4/2020 | Chao |
| 2020/0129143 | A1 | 4/2020 | Di Tullio |
| 2020/0129144 | A1 | 4/2020 | Rajguru |
| 2020/0129147 | A1 | 4/2020 | Nair |
| 2020/0129148 | A1 | 4/2020 | Jenkins |
| 2020/0129158 | A1 | 4/2020 | Chao |
| 2020/0129159 | A1 | 4/2020 | Rajguru |
| 2020/0375576 | A1 | 12/2020 | Moulton |

FOREIGN PATENT DOCUMENTS

| | | |
|---|---|---|
| WO | 2022238092 A1 | 11/2022 |
| WO | 2022238276 A1 | 11/2022 |
| WO | 2022238392 A1 | 11/2022 |

OTHER PUBLICATIONS

Wang, Peng et al "Image-Based Co-Registration of Angiography and Intravascular Ultrasound Images" IEEE Transactions on Medicla Imaging, vol. 32, No. 12, Dec. 2013, pp. 2238-2249.

* cited by examiner

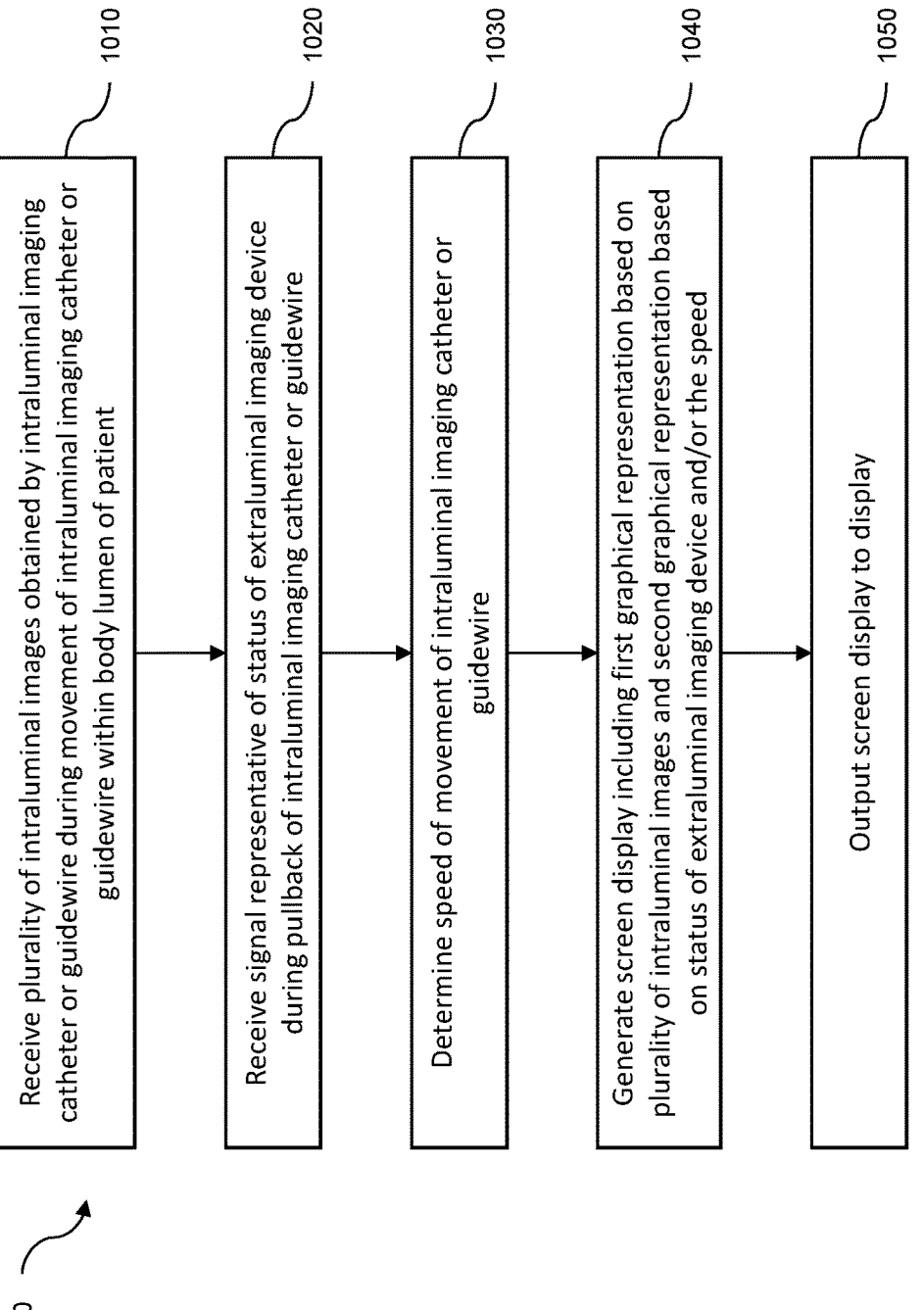

1000

1010
Receive plurality of intraluminal images obtained by intraluminal imaging catheter or guidewire during movement of intraluminal imaging catheter or guidewire within body lumen of patient 1020
Receive signal representative of status of extraluminal imaging device during pullback of intraluminal imaging catheter or guidewire 1030
Determine speed of movement of intraluminal imaging catheter or guidewire 1040
Generate screen display including first graphical representation based on plurality of intraluminal images and second graphical representation based on status of extraluminal imaging device and/or the speed 1050
Output screen display to display

Fig. 10

COREGISTRATION RELIABILITY WITH EXTRALUMINAL IMAGE AND INTRALUMINAL DATA

TECHNICAL FIELD

The present disclosure relates generally to co-registering intraluminal (e.g., intravascular data) with extraluminal (e.g., x-ray) imaging data. For example, the reliability of the co-registration can be determined based on the x-ray imaging during intravascular data acquisition and an indication of the determined reliability can be displayed with the intravascular data.

BACKGROUND

Physicians use many different medical diagnostic systems and tools to monitor a patient's health and diagnose and treat medical conditions. Different modalities of medical diagnostic systems may provide a physician with different images, models, and/or data relating to internal structures within a patient. These modalities include invasive devices and systems, such as intravascular systems, and non-invasive devices and systems, such as external ultrasound systems or x-ray systems. Using multiple diagnostic systems to examine a patient's anatomy provides a physician with added insight into the condition of the patient.

In the field of intravascular imaging and physiology measurement, co-registration of data from invasive devices (e.g. intravascular ultrasound (IVUS) devices) with images collected non-invasively (e.g. via x-ray angiography and/or x-ray venography) is a powerful technique for improving the efficiency and accuracy of vascular catheterization procedures. Co-registration identifies the locations of intravascular data measurements along a blood vessel by mapping the data to an angiography image of the vessel. A physician may then see on an angiography image exactly where along the vessel a measurement was made, rather than estimate the location.

A user viewing coregistered intravascular data with x-ray imaging data must ensure that several conditions are met throughout an imaging procedure. Specifically, the intravascular device must not be moved too quickly through the blood vessel, and the user must ensure that fluoroscopy images and intravascular data are acquired simultaneously to ensure that coregistration is successful. If either of these conditions are not met throughout the imaging procedure, coregistration may be impossible or inaccurate. In some cases, the user may then be required to reacquire intravascular data from sections of the vessel, sometimes requiring a patient to undergo additional intravascular procedures.

SUMMARY

Embodiments of the present disclosure are systems, devices, and methods for assessing the reliability of coregistration between intraluminal data and extraluminal images. For example, the intraluminal data can be intravascular imaging data, such as intravascular ultrasound (IVUS) images. The extraluminal images can be x-ray images. A processor circuit can determine whether x-ray fluoroscopy images are being simultaneously obtained while the IVUS images are being obtained. If not, coregistration is not possible. The processor circuit can also determine if the IVUS catheter is moving too quickly through the blood vessel. If so, the coregistration may be inaccurate. The processor circuit generates and outputs a graphical indication of the coregistration reliability assessment, which is based on an operational state of the x-ray imaging device and/or the speed that the IVUS catheter moves, to a display. For example, the graphical representation can be provided over or adjacent to a longitudinal view of the vessel that is generated based on the IVUS images, e.g., as the IVUS images are acquired. This longitudinal view may be an ILD (in line digital or image longitudinal display). This advantageously provides real time or near real time guidance to a user, such as a physician or other clinical professional, to immediately remedy any issues preventing accurate coregistration. This also allows the user to identify regions where IVUS images and/or fluoroscopy images were not properly acquired during the procedure, rather than after the procedure is completed. The user may then immediately reimage any problematic regions ensuring that all relevant areas of the vessel are imaged in a single imaging procedure and the procedure is completed as quickly as possible, while also allowing coregistration to be accurately completed.

In one aspect, the coregistration system displays a coregistration reliability indicator to the user if IVUS images are being collected but no x-ray fluoroscopy images are being simultaneously collected. This indicator provides guidance to the user to begin to acquire fluoroscopy images. The coregistration system may also identify any regions along the longitudinal view of the vessel where IVUS data was collected without corresponding fluoroscopy images.

In another aspect, the coregistration system displays a coregistration reliability indicator to the user if the IVUS catheter is moving too quickly through the vessel to acquire accurate intravascular data or coregister the IVUS images with corresponding fluoroscopy images. The user may then slow the speed of the IVUS catheter. The system may also identify any regions along the longitudinal view of the vessel where the IVUS catheter was moved too quickly.

In an exemplary aspect, a system is provided. The system comprises a processor circuit configured for communication with an extraluminal imaging device and an intraluminal imaging catheter or guidewire, wherein the processor circuit is configured to receive a plurality of intraluminal images obtained by the intraluminal imaging catheter or guidewire during movement of the intraluminal imaging catheter or guidewire within a body lumen of a patient; receive a signal representative of a status of the extraluminal imaging device during the movement of the intraluminal imaging catheter or guidewire; generate a screen display comprising a first graphical representation based on the plurality of intraluminal images; and a second graphical representation based on the status of the extraluminal imaging device, wherein the first graphical representation and the second graphical representation are positioned proximate to one another; and output the screen display to a display in communication with the processor circuit.

In one aspect, the second graphical representation is configured to indicate that the plurality of intraluminal images cannot be co-registered to an extraluminal image in response to the status of extraluminal imaging device comprising an inactive status. In one aspect, wherein the first graphical representation comprises a longitudinal view of the body lumen. In one aspect, the longitudinal view of the body lumen comprises a stack of the plurality of intraluminal images. In one aspect, the second graphical representation is positioned at a border of the longitudinal view. In one aspect, the second graphical representation comprises a plurality of symbols positioned along the border. In one aspect, the second graphical representation comprises an overlay on the longitudinal view. In one aspect, a length of the overlay is representative of at least one of a distance or a time during the movement of the intraluminal imaging catheter or guidewire that corresponds to the status of the extraluminal imaging device. In one aspect, the second graphical representation comprises the overlay in response to the status of the extraluminal imaging device comprising an inactive status. In one aspect, the processor circuit is configured to determine a speed of the movement of the intraluminal imaging catheter or guidewire; and the second graphical representation is further based on the speed. In one aspect, the second graphical representation is configured to indicate that the plurality of intraluminal images can be co-registered to an extraluminal image in response to the status of extraluminal imaging device comprising an active status; and the speed satisfying a threshold. In one aspect, the second graphical representation is configured to indicate decreased reliability in co-registration of the plurality of intraluminal images to an extraluminal image in response to the status of extraluminal imaging device comprising an active status; and the speed not satisfying a threshold. In one aspect, the second graphical representation is color-coded based on at least one of the status of the extraluminal imaging device or the speed. In one aspect, the second graphical representation comprises text. In one aspect, the screen display comprises a plurality of second graphical representations.

In an exemplary aspect, a system is provided. The system comprises an intravascular ultrasound (IVUS) imaging catheter; and a processor circuit configured for communication with an x-ray imaging device and the IVUS catheter, wherein the processor circuit is configured to receive a plurality of IVUS images obtained by the IVUS catheter during a pullback of the IVUS catheter within a blood vessel of a patient; receive a signal representative of a status of the x-ray imaging device during the pullback of the IVUS catheter, wherein the status comprises one of an active status in which the x-ray imaging device is obtaining x-ray fluoroscopic images of the pullback; or an inactive status in which the x-ray imaging device is not obtaining x-ray fluoroscopic images of the pullback; determine a speed of the movement of the IVUS catheter; generate a screen display comprising a longitudinal view of the blood vessel based on the plurality of IVUS images; and one or more color-coded graphical representations based on at least one of the status of the x-ray imaging device or the speed, wherein the one or more graphical representations are positioned over or adjacent to the longitudinal view, and wherein the one or more color-coded graphical representations comprise at least one of an indication that the plurality of IVUS images cannot be co-registered to an x-ray image; an indication that the plurality of IVUS images can be co-registered to the x-ray image; or an indication of decreased reliability in co-registration of the plurality of IVUS images to the x-ray image; and output the screen display to a display in communication with the processor circuit.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 10 is a flow diagram for a method of coregistration, according to aspects of the present disclosure.

DETAILED DESCRIPTION

Figure 1:
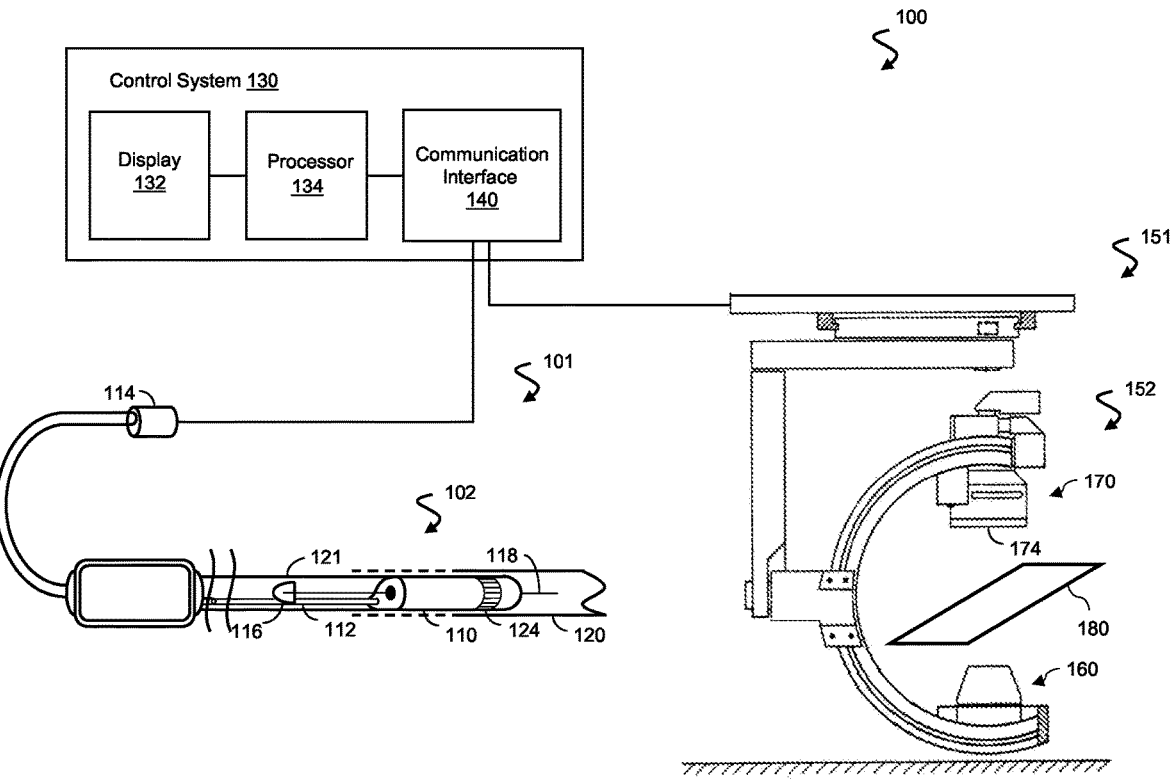
FIG. 1 is a schematic diagram of an intraluminal imaging and x-ray system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The devices, systems, and methods described herein can include one or more features described in U.S. Provisional Application No. 63/187,964, filed May 13, 2021, and titled "Pathway Modification for Coregistration of Extraluminal Image and Intraluminal Data" (Atty Dkt No. 2021PF00091/44755.2199PV01), U.S. Provisional Application No. 63/187,983, filed May 13, 2021, and titled "Coregistration of Intraluminal Data to a Guidewire in Extraluminal Image Obtained Without Contrast" (Atty Dkt No. 2021PF00092/44755.2200PV01), U.S. Provisional Application No. 63/187,990, filed May 13, 2021, and titled "Preview of Intraluminal Ultrasound Image Along Longitudinal View of Body Lumen" (Atty Dkt No. 2021PF00093/44755.2201PV01), U.S. Provisional Application No. 63/187,961, filed May 13, 2021, and titled "Intraluminal Treatment Guidance from Prior Extraluminal Imaging, Intraluminal Data, and Coregistration" (Atty Dkt No.

2021PF00012/44755.2192PV01), each of which is incorporated by reference herein in its entirety.

The devices, systems, and methods described herein can also include one or more features described in European Application No. 21154591.8, filed Feb. 1, 2021, and titled "X-Ray and Intravascular Ultrasound Image Registration", which is incorporated by reference herein in its entirety.

The devices, systems, and methods described herein can also include one or more features described in U.S. Publication No. 2020/0129144, titled "Disease Specific and Treatment Type Specific Control of Intraluminal Ultrasound Imaging", U.S. Publication No. 2020/0129142, titled "Intraluminal Ultrasound Navigation Guidance and Associated Devices, Systems, And Methods", U.S. Publication No. 2020/0129148, titled "Intraluminal Ultrasound Imaging with Automatic and Assisted Labels And Bookmarks", U.S. Publication No. 2020/0129158, titled "Graphical Longitudinal Display for Intraluminal Ultrasound Imaging and Associated Devices, Systems, and Methods", U.S. Publication No. 2020/0129147, titled "Intraluminal Ultrasound Vessel Border Selection and Associated Devices, Systems, and Methods", U.S. Publication No. 2020/0129159, titled "Intraluminal Ultrasound Directional Guidance and Associated Devices, Systems, and Methods", U.S. Publication No. 2020/0129143, titled "Speed Determination for Intraluminal Ultrasound Imaging and Associated Devices, Systems, And Methods", each of which is incorporated by reference herein in its entirety.

FIG. 1 is a schematic diagram of an intraluminal imaging and x-ray system 100, according to aspects of the present disclosure. In some embodiments, the intraluminal imaging and x-ray system 100 may include two separate systems or be a combination of two systems: an intraluminal sensing system 101 and an extraluminal imaging system 151. The intraluminal sensing system 101 obtains medical data about a patient's body while the intraluminal device 102 is positioned inside the patient's body. For example, the intraluminal sensing system 101 can control the intraluminal device 102 to obtain intraluminal images of the inside of the patient's body while the intraluminal device 102 is inside the patient's body. The extraluminal imaging system 151 obtains medical data about the patient's body while the extraluminal imaging device 152 is positioned outside the patient's body. For example, the extraluminal imaging system 151 can control extraluminal imaging device 152 to obtain extraluminal images of the inside of the patient's body while the extraluminal imaging device 152 is outside the patient's body.

The intraluminal imaging system 101 may be in communication with the extraluminal imaging system 151 through any suitable components. Such communication may be established through a wired cable, through a wireless signal, or by any other means. In addition, the intraluminal imaging system 101 may be in continuous communication with the x-ray system 151 or may be in intermittent communication. For example, the two systems may be brought into temporary communication via a wired cable, or brought into communication via a wireless communication, or through any other suitable means at some point before, after, or during an examination. In addition, the intraluminal system 101 may receive data such as x-ray images, annotated x-ray images, metrics calculated with the x-ray imaging system 151, information regarding dates and times of examinations, types and/or severity of patient conditions or diagnoses, patient history or other patient information, or any suitable data or information from the x-ray imaging system 151. The x-ray imaging system 151 may also receive any of these data from the intraluminal imaging system 101. In some embodiments, and as shown in FIG. 1, the intraluminal imaging system 101 and the x-ray imaging system 151 may be in communication with the same control system 130. In this embodiment, both systems may be in communication with the same display 132, processor 134, and communication interface 140 shown as well as in communication with any other components implemented within the control system 130.

In some embodiments, the system 100 may not include a control system 130 in communication with the intraluminal imaging system 101 and the x-ray imaging system 151. Instead, the system 100 may include two separate control systems. For example, one control system may be in communication with or be a part of the intraluminal imaging system 101 and an additional separate control system may be in communication with or be a part of the x-ray imaging system 151. In this embodiment, the separate control systems of both the intraluminal imaging system 101 and the x-ray imaging system 151 may be similar to the control system 130. For example, each control system may include various components or systems such as a communication interface, processor, and/or a display. In this embodiment, the control system of the intraluminal imaging system 101 may perform any or all of the coregistration steps described in the present disclosure. Alternatively, the control system of the x-ray imaging system 151 may perform the coregistration steps described.

The intraluminal imaging system 101 can be an ultrasound imaging system. In some instances, the intraluminal imaging system 101 can be an intravascular ultrasound (IVUS) imaging system. The intraluminal imaging system 101 may include an intraluminal imaging device 102, such as a catheter, guide wire, or guide catheter, in communication with the control system 130. The control system 130 may include a display 132, a processor 134, and a communication interface 140 among other components. The intraluminal imaging device 102 can be an ultrasound imaging device. In some instances, the device 102 can be an IVUS imaging device, such as a solid-state IVUS device.

At a high level, the IVUS device 102 emits ultrasonic energy from a transducer array 124 included in a scanner assembly, also referred to as an IVUS imaging assembly, mounted near a distal end of the catheter device. The ultrasonic energy is reflected by tissue structures in the surrounding medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The communication interface 140 transfers the received echo signals to the processor 134 of the control system 130 where the ultrasound image (including flow information in some embodiments) is reconstructed and displayed on the display 132. The control system 130, including the processor 134, can be operable to facilitate the features of the IVUS imaging system 101 described herein. For example, the processor 134 can execute computer readable instructions stored on the non-transitory tangible computer readable medium.

The communication interface 140 facilitates communication of signals between the control system 130 and the scanner assembly 110 included in the IVUS device 102. This communication includes the steps of: (1) providing commands to integrated circuit controller chip(s) included in the scanner assembly 110 to select the particular transducer array element(s), or acoustic element(s), to be used for transmit and receive, (2) providing the transmit trigger signals to the integrated circuit controller chip(s) included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) of the scanner assembly 110. In some embodiments, the communication interface 140 performs preliminary processing of the echo data prior to relaying the data to the processor 134. In examples of such embodiments, the communication interface 140 performs amplification, filtering, and/or aggregating of the data. In an embodiment, the communication interface 140 also supplies high- and low-voltage DC power to support operation of the device 102 including circuitry within the scanner assembly 110.

The processor 134 receives the echo data from the scanner assembly 110 by way of the communication interface 140 and processes the data to reconstruct an image of the tissue structures in the medium surrounding the scanner assembly 110. The processor 134 outputs image data such that an image of the lumen 120, such as a cross-sectional image of the vessel 120, is displayed on the display 132. The lumen 120 may represent fluid filled or surrounded structures, both natural and man-made. The lumen 120 may be within a body of a patient. The lumen 120 may be a blood vessel, such as an artery or a vein of a patient's vascular system, including cardiac vasculature, peripheral vasculature, neural vasculature, renal vasculature, and/or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

In some embodiments, the IVUS device includes some features similar to traditional solid-state IVUS catheters, such as the EagleEye® catheter, Visions PV 0.014P RX catheter, Visions PV 0.018 catheter, Visions PV 0.035, and Pioneer Plus catheter, each of which are available from Koninklijke Philips N. V, and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a patient interface module (PIM) connector 114 at a proximal end of the device 102. The PIM connector 114 electrically couples the transmission line bundle 112 to the communication interface 140 and physically couples the IVUS device 102 to the communication interface 140. In some embodiments, the communication interface 140 may be a PIM. In an embodiment, the IVUS device 102 further includes a guide wire exit port 116. Accordingly, in some instances the IVUS device 102 is a rapid-exchange catheter. The guide wire exit port 116 allows a guide wire 118 to be inserted towards the distal end to direct the device 102 through the vessel 120.

In some embodiments, the intraluminal imaging device 102 may acquire intravascular images of any suitable imaging modality, including optical coherence tomography (OCT) and intravascular photoacoustic (IVPA).

In some embodiments, the intraluminal device 102 is a pressure sensing device (e.g., pressure-sensing guidewire) that obtains intraluminal (e.g., intravascular) pressure data, and the intraluminal system 101 is an intravascular pressure sensing system that determines pressure ratios based on the pressure data, such as fractional flow reserve (FFR), instantaneous wave-free ratio (iFR), and/or other suitable ratio between distal pressure and proximal/aortic pressure (Pd/Pa). In some embodiments, the intraluminal device 102 is a flow sensing device (e.g., flow-sensing guidewire) that obtains intraluminal (e.g., intravascular) flow data, and the intraluminal system 101 is an intravascular flow sensing system that determines flow-related values based on the flow data, such as coronary flow reserve (CFR), flow velocity, flow volume, etc.

The x-ray imaging system 151 may include an x-ray imaging apparatus or device 152 configured to perform x-ray imaging, angiography, fluoroscopy, radiography, venography, among other imaging techniques. The x-ray imaging system 151 can generate a single x-ray image (e.g., an angiogram or venogram) or multiple (e.g., two or more) x-ray images (e.g., a video and/or fluoroscopic image stream) based on x-ray image data collected by the x-ray device 152. The x-ray imaging device 152 may be of any suitable type, for example, it may be a stationary x-ray system such as a fixed c-arm x-ray device, a mobile c-arm x-ray device, a straight arm x-ray device, or a u-arm device. The x-ray imaging device 152 may additionally be any suitable mobile device. The x-ray imaging device 152 may also be in communication with the control system 130. In some embodiments, the x-ray system 151 may include a digital radiography device or any other suitable device.

The x-ray device 152 as shown in FIG. 1 includes an x-ray source 160 and an x-ray detector 170 including an input screen 174. The x-ray source 160 and the detector 170 may be mounted at a mutual distance. Positioned between the x-ray source 160 and the x-ray detector 170 may be an anatomy of a patient or object 180. For example, the anatomy of the patient (including the vessel 120) can be positioned between the x-ray source 160 and the x-ray detector 170.

The x-ray source 160 may include an x-ray tube adapted to generate x-rays. Some aspects of the x-ray source 160 may include one or more vacuum tubes including a cathode in connection with a negative lead of a high-voltage power source and an anode in connection with a positive lead of the same power source. The cathode of the x-ray source 160 may additionally include a filament. The filament may be of any suitable type or constructed of any suitable material, including tungsten or rhenium tungsten, and may be positioned within a recessed region of the cathode. One function of the cathode may be to expel electrons from the high voltage power source and focus them into a well-defined beam aimed at the anode. The anode may also be constructed of any suitable material and may be configured to create x-radiation from the emitted electrons of the cathode. In addition, the anode may dissipate heat created in the process of generating x-radiation. The anode may be shaped as a beveled disk and, in some embodiments, may be rotated via an electric motor. The cathode and anode of the x-ray source 160 may be housed in an airtight enclosure, sometimes referred to as an envelope.

In some embodiments, the x-ray source 160 may include a radiation object focus which influences the visibility of an image. The radiation object focus may be selected by a user of the system 100 or by a manufacture of the system 100 based on characteristics such as blurring, visibility, heat-dissipating capacity, or other characteristics. In some embodiments, an operator or user of the system 100 may switch between different provided radiation object foci in a point-of-care setting.

The detector 170 may be configured to acquire x-ray images and may include the input screen 174. The input screen 174 may include one or more intensifying screens configured to absorb x-ray energy and convert the energy to light. The light may in turn expose a film. The input screen 174 may be used to convert x-ray energy to light in embodiments in which the film may be more sensitive to light than x-radiation. Different types of intensifying screens within the image intensifier may be selected depending on the region of a patient to be imaged, requirements for image detail and/or patient exposure, or any other factors. Intensifying screens may be constructed of any suitable materials, including barium lead sulfate, barium strontium sulfate, barium fluorochloride, yttrium oxysulfide, or any other suitable material. The input screen 374 may be a fluorescent screen or a film positioned directly adjacent to a fluorescent screen. In some embodiments, the input screen 374 may also include a protective screen to shield circuitry or components within the detector 370 from the surrounding environment. In some embodiments, the x-ray detector 170 may include a flat panel detector (FPD). The detector 170 may be an indirect conversion FPD or a direct conversion FPD. The detector 170 may also include charge-coupled devices (CCDs). The x-ray detector 370 may additionally be referred to as an x-ray sensor.

The object 180 may be any suitable object to be imaged. In an exemplary embodiment, the object may be the anatomy of a patient. More specifically, the anatomy to be imaged may include chest, abdomen, the pelvic region, neck, legs, head, feet, a region with cardiac vasculature, or a region containing the peripheral vasculature of a patient and may include various anatomical structures such as, but not limited to, organs, tissue, blood vessels and blood, gases, or any other anatomical structures or objects. In other embodiments, the object may be or include man-made structures.

In some embodiments, the x-ray imaging system 151 may be configured to obtain x-ray images without contrast. In some embodiments, the x-ray imaging system 151 may be configured to obtain x-ray images with contrast (e.g., angiogram or venogram). In such embodiments, a contrast agent or x-ray dye may be introduced to a patient's anatomy before imaging. The contrast agent may also be referred to as a radiocontrast agent, contrast material, contrast dye, or contrast media. The contrast dye may be of any suitable material, chemical, or compound and may be a liquid, powder, paste, tablet, or of any other suitable form. For example, the contrast dye may be iodine-based compounds, barium sulfate compounds, gadolinium-based compounds, or any other suitable compounds. The contrast agent may be used to enhance the visibility of internal fluids or structures within a patient's anatomy. The contrast agent may absorb external x-rays, resulting in decreased exposure on the x-ray detector 170.

In some embodiments, the extraluminal imaging system 151 could be any suitable extraluminal imaging device, such as computed tomography (CT) or magnetic resonance imaging (MRI).

When the control system 130 is in communication with the x-ray system 151, the communication interface 140 facilitates communication of signals between the control system 130 and the x-ray device 152. This communication includes providing control commands to the x-ray source 160 and/or the x-ray detector 170 of the x-ray device 152 and receiving data from the x-ray device 152. In some embodiments, the communication interface 140 performs preliminary processing of the x-ray data prior to relaying the data to the processor 134. In examples of such embodiments, the communication interface 140 may perform amplification, filtering, and/or aggregating of the data. In an embodiment, the communication interface 140 also supplies high- and low-voltage DC power to support operation of the device 152 including circuitry within the device.

The processor 134 receives the x-ray data from the x-ray device 152 by way of the communication interface 140 and processes the data to reconstruct an image of the anatomy being imaged. The processor 134 outputs image data such that an image is displayed on the display 132. In an embodiment in which the contrast agent is introduced to the anatomy of a patient and a venogram is to be generated, the particular areas of interest to be imaged may be one or more blood vessels or other section or part of the human vasculature. The contrast agent may identify fluid filled structures, both natural and/or man-made, such as arteries or veins of a patient's vascular system, including cardiac vasculature, peripheral vasculature, neural vasculature, renal vasculature, and/or any other suitable lumen inside the body. For example, the x-ray device 152 may be used to examine any number of anatomical locations and tissue types, including without limitation all the organs, fluids, or other structures or parts of an anatomy previously mentioned. In addition to natural structures, the x-ray device 152 may be used to examine man-made structures such as any of the previously mentioned structures.

The processor 134 may be configured to receive an x-ray image that was stored by the x-ray imaging device 152 during a clinical procedure. The images may be further enhanced by other information such as patient history, patient record, IVUS imaging, pre-operative ultrasound imaging, pre-operative CT, or any other suitable data.

Figure 2:
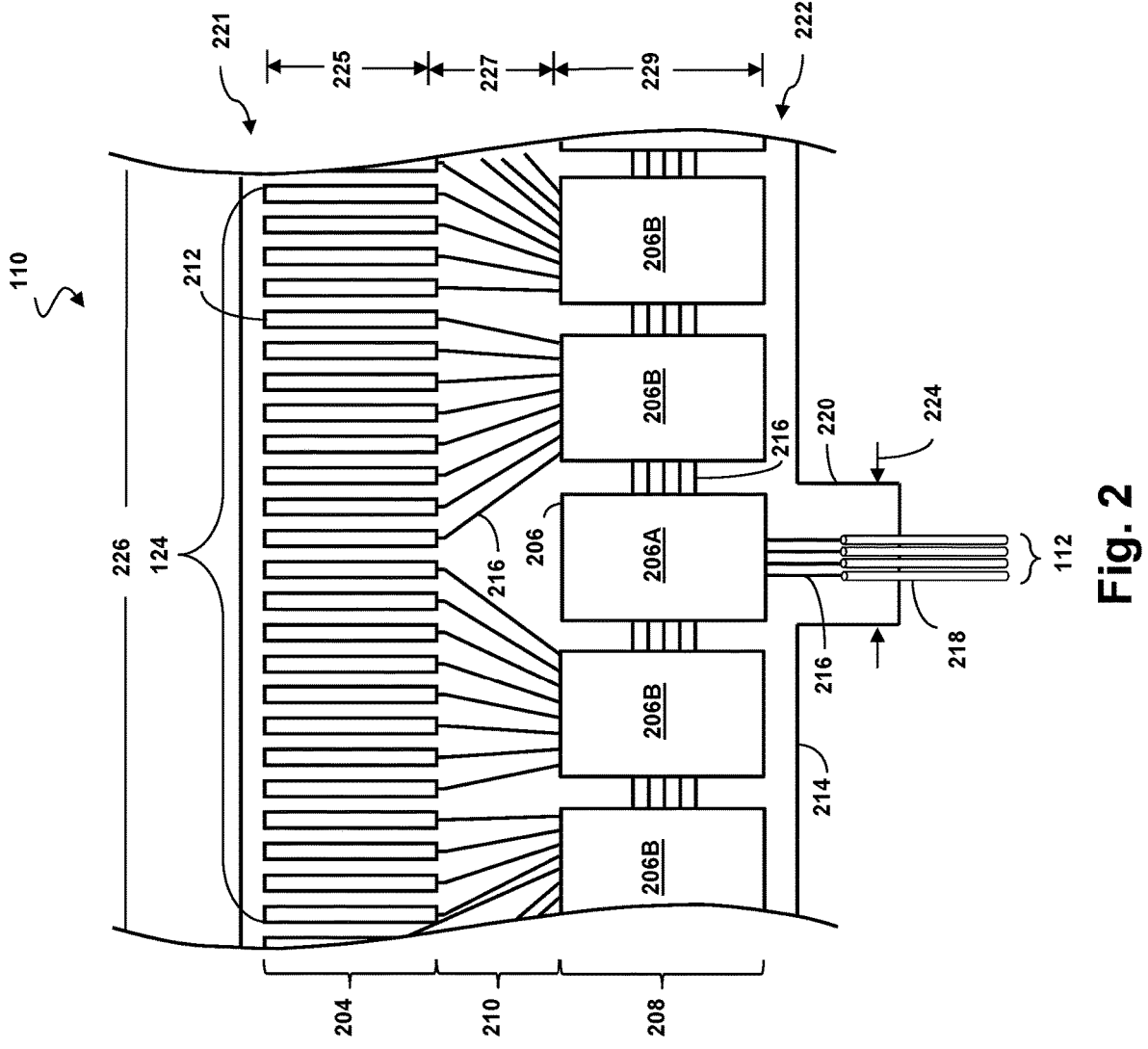
FIG. 2 is a diagrammatic top view of an ultrasound imaging assembly in a flat configuration, according to aspects of the present disclosure.

FIG. 2 is a diagrammatic top view of a portion of a flexible assembly 110, according to aspects of the present disclosure. The flexible assembly 110 includes a transducer array 124 formed in a transducer region 204 and transducer control logic dies 206 (including dies 206A and 206B) formed in a control region 208, with a transition region 210 disposed therebetween. The transducer array 124 includes an array of ultrasound transducer elements 212. The transducer control logic dies 206 are mounted on a flexible substrate 214 into which the transducer elements 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducer elements 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 μm and 100 μm, with some particular embodiments being between 5 μm and 25.1 μm, e.g., 6 μm.

The set of transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 112, between a processing system, e.g., processing system 106, and the flexible assembly 110. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a plurality of transducer elements 512 positioned on a transducer element 212 to emit an ultrasonic signal and selects a transducer element 212 to receive an echo. In the depicted embodiment, the master controller 206A does not directly control any transducer elements 212. In other embodiments, the master controller 206A drives the same number of transducer elements 212 as the slave controllers 206B or drives a reduced set of transducer elements 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducer elements 212, in an embodiment, the flexible substrate 214 includes conductive traces 216 formed in the film layer that carry signals between the control logic dies 206 and the transducer elements 212. In particular, the conductive traces 216 providing communication between the control logic dies 206 and the transducer elements 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 μm. For example, in an embodiment, 5 μm conductive traces 216 are separated by 5 μm of space. The width of a conductive trace 216 on the flexible substrate may be further determined by the width of the conductor 218 to be coupled to the trace or pad.

The flexible substrate 214 can include a conductor interface 220 in some embodiments. The conductor interface 220 can be in a location of the flexible substrate 214 where the conductors 218 of the cable 112 are coupled to the flexible substrate 214. For example, the bare conductors of the cable 112 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
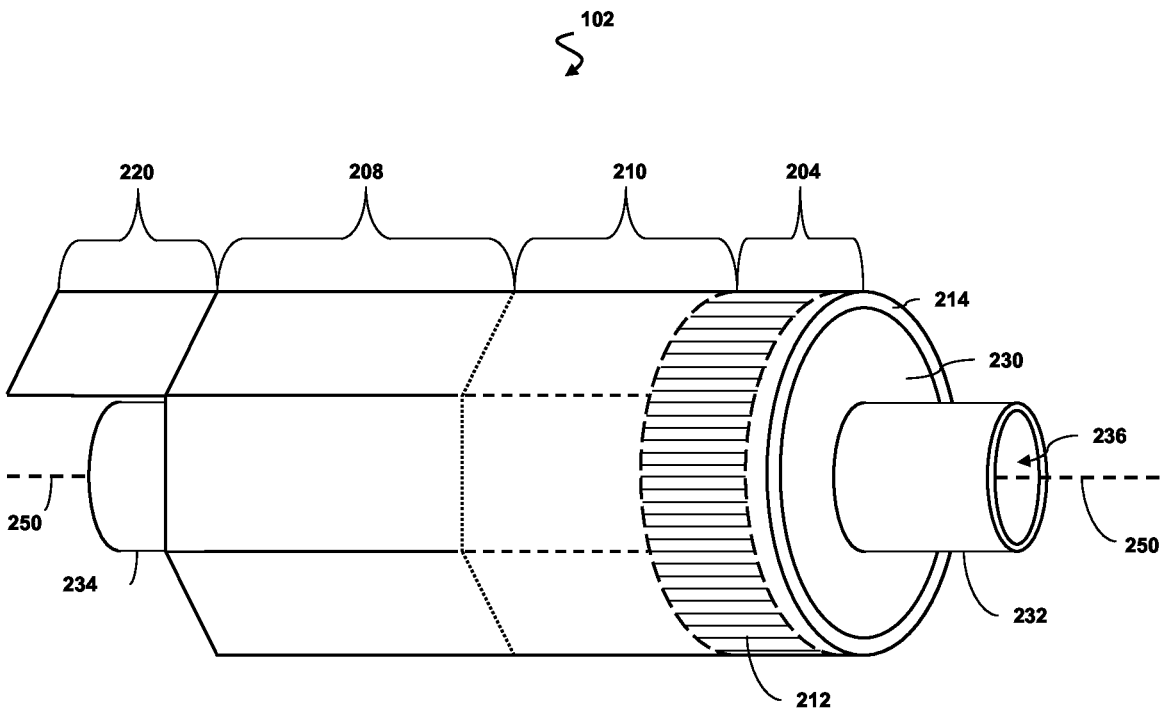
FIG. 3 is a diagrammatic perspective view of the ultrasound imaging assembly shown in FIG. 2 in a rolled configuration around a support member, according to aspects of the present disclosure.

FIG. 3 illustrates a perspective view of the scanner assembly 110 in a rolled configuration. In some instances, the flexible substrate 214 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

Depending on the application and embodiment of the presently disclosed invention, transducer elements 212 may be piezoelectric transducers, single crystal transducer, or PZT (lead zirconate titanate) transducers. In other embodiments, the transducer elements of transducer array 124 may be flexural transducers, piezoelectric micromachined ultrasonic transducers (PMUTs), capacitive micromachined ultrasonic transducers (CMUTs), or any other suitable type of transducer element. In such embodiments, transducer elements 212 may comprise an elongate semiconductor material or other suitable material that allows micromachining or similar methods of disposing extremely small elements or circuitry on a substrate.

In some embodiments, the transducer elements 212 and the controllers 206 can be positioned in an annular configuration, such as a circular configuration or in a polygon configuration, around a longitudinal axis 250 of a support member 230. It is understood that the longitudinal axis 250 of the support member 230 may also be referred to as the longitudinal axis of the scanner assembly 110, the flexible elongate member 121, or the device 102. For example, a cross-sectional profile of the imaging assembly 110 at the transducer elements 212 and/or the controllers 206 can be a circle or a polygon. Any suitable annular polygon shape can be implemented, such as one based on the number of controllers or transducers, flexibility of the controllers or transducers, etc. Some examples may include a pentagon, hexagon, heptagon, octagon, nonagon, decagon, etc. In some examples, the transducer controllers 206 may be used for controlling the ultrasound transducers 512 of transducer elements 212 to obtain imaging data associated with the vessel 120.

The support member 230 can be referenced as a unibody in some instances. The support member 230 can be composed of a metallic material, such as stainless steel, or a non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. In some embodiments, support member 230 may be composed of 303 stainless steel. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process or a micro injection molding process.

Figure 4:
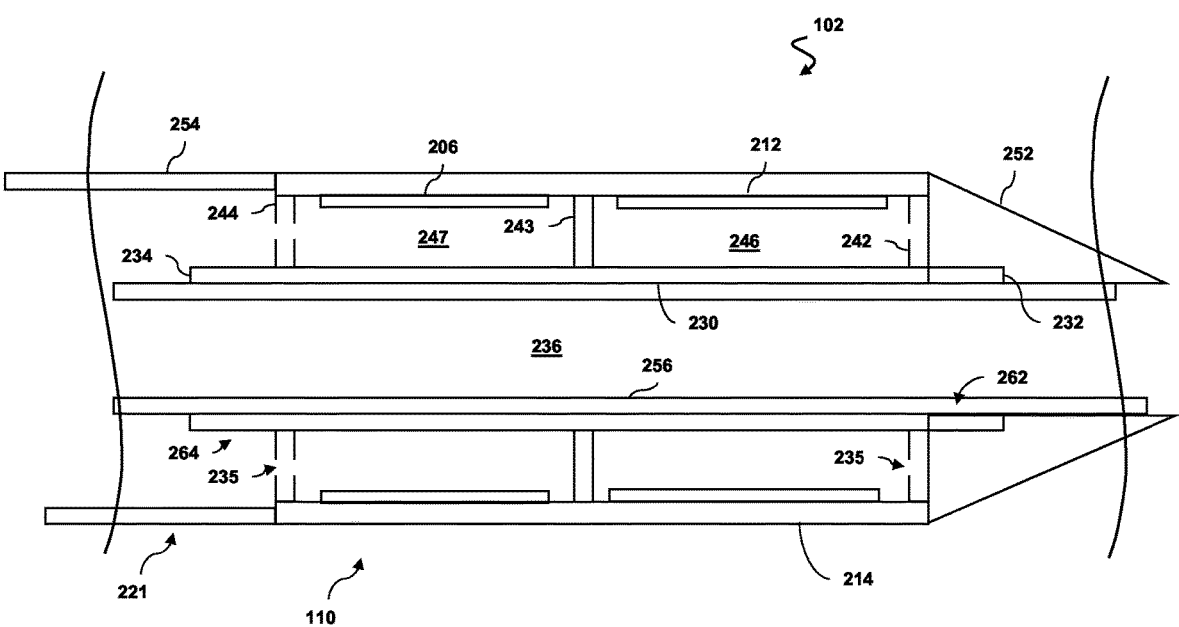
FIG. 4 is a diagrammatic cross-sectional side view of the ultrasound imaging assembly shown in FIG. 3, according to aspects of the present disclosure.

Referring now to FIG. 4, shown therein is a diagrammatic cross-sectional side view of a distal portion of the intraluminal imaging device 102, including the flexible substrate 214 and the support member 230, according to aspects of the present disclosure. The lumen 236 may be connected with the entry/exit port 116 and is sized and shaped to receive the guide wire 118 (FIG. 1). In some embodiments, the support member 230 may be integrally formed as a unitary structure, while in other embodiments the support member 230 may be formed of different components, such as a ferrule and stands 242, 243, and 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 243, and 244 that extend vertically are provided at the distal, central, and proximal portions respectively, of the support member 230. The stands 242, 243, and 244 elevate and support the distal, central, and proximal portions of the flexible substrate 214. In that regard, portions of the flexible substrate 214, such as the transducer portion 204 (or transducer region 204), can be spaced from a central body portion of the support member 230 extending between the stands 242, 243, and 244. The stands 242, 243, 244 can have the same outer diameter or different outer diameters. For example, the distal stand 242 can have a larger or smaller outer diameter than the central stand 243 and/or proximal stand 244 and can also have special features for rotational alignment as well as control chip placement and connection.

To improve acoustic performance, the cavity between the transducer array 212 and the surface of the support member 230 may be filled with an acoustic backing material 246. The liquid backing material 246 can be introduced between the flexible substrate 214 and the support member 230 via passageway 235 in the stand 242, or through additional recesses as will be discussed in more detail hereafter. The backing material 246 may serve to attenuate ultrasound energy emitted by the transducer array 212 that propagates in the undesired, inward direction.

The cavity between the circuit controller chips 206 and the surface of the support member 230 may be filled with an underfill material 247. The underfill material 247 may be an adhesive material (e.g. an epoxy) which provides structural support for the circuit controller chips 206 and/or the flexible substrate 214. The underfill 247 may additionally be any suitable material.

In some embodiments, the central body portion of the support member can include recesses allowing fluid communication between the lumen of the unibody and the cavities between the flexible substrate 214 and the support member 230. Acoustic backing material 246 and/or underfill material 247 can be introduced via the cavities (during an assembly process, prior to the inner member 256 extending through the lumen of the unibody. In some embodiments, suction can be applied via the passageways 235 of one of the stands 242, 244, or to any other suitable recess while the liquid backing material 246 is fed between the flexible substrate 214 and the support member 230 via the passageways 235 of the other of the stands 242, 244, or any other suitable recess. The backing material can be cured to allow it to solidify and set. In various embodiments, the support member 230 includes more than three stands 242, 243, and 244, only one or two of the stands 242, 243, 244, or none of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions of the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the proximal end of flexible substrate 214. A distal tip member 252 is coupled to the distal portion 262 of the support member 230. For example, the distal member 252 is positioned around the distal flange 232. The tip member 252 can abut and be in contact with the distal end of flexible substrate 214 and the stand 242. In other embodiments, the proximal end of the tip member 252 may be received within the distal end of the flexible substrate 214 in its rolled configuration. In some embodiments there may be a gap between the flexible substrate 214 and the tip member 252. The distal member 252 can be the distal-most component of the intraluminal imaging device 102. The distal tip member 252 may be a flexible, polymeric component that defines the distal-most end of the imaging device 102. The distal tip member 252 may additionally define a lumen in communication with the lumen 236 defined by support member 230. The guide wire 118 may extend through lumen 236 as well as the lumen defined by the tip member 252.

One or more adhesives can be disposed between various components at the distal portion of the intraluminal imaging device 102. For example, one or more of the flexible substrate 214, the support member 230, the distal member 252, the proximal inner member 256, the transducer array 212, and/or the proximal outer member 254 can be coupled to one another via an adhesive. Stated differently, the adhesive can be in contact with e.g. the transducer array 212, the flexible substrate 214, the support member 230, the distal member 252, the proximal inner member 256, and/or the proximal outer member 254, among other components.

Figure 5:
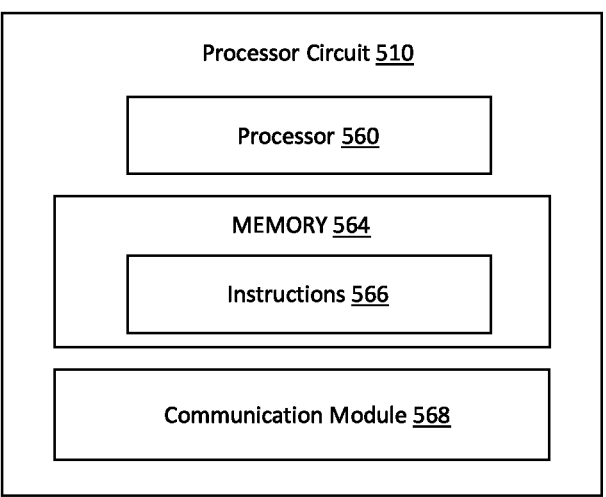
FIG. 5 is a schematic diagram of a processor circuit, according to aspects of the present disclosure.

FIG. 5 is a schematic diagram of a processor circuit, according to aspects of the present disclosure. The processor circuit 510 may be implemented in the control system 130 of FIG. 1, the intraluminal imaging system 101, and/or the x-ray imaging system 151, or any other suitable location. In an example, the processor circuit 510 may be in communication with intraluminal imaging device 102, the x-ray imaging device 152, the display 132 within the system 100. The processor circuit 510 may include the processor 134 and/or the communication interface 140 (FIG. 1). One or more processor circuits 510 are configured to execute the operations described herein. As shown, the processor circuit 510 may include a processor 560, a memory 564, and a communication module 568. These elements may be in direct or indirect communication with each other, for example via one or more buses.

The processor 560 may include a CPU, a GPU, a DSP, an application-specific integrated circuit (ASIC), a controller, an FPGA, another hardware device, a firmware device, or any combination thereof configured to perform the operations described herein. The processor 560 may also be implemented as a combination of computing devices, e.g., a combination of a DSP and a microprocessor, a plurality of microprocessors, one or more microprocessors in conjunction with a DSP core, or any other such configuration.

The memory 564 may include a cache memory (e.g., a cache memory of the processor 560), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 564 includes a non-transitory computer-readable medium. The memory 564 may store instructions 566. The instructions 566 may include instructions that, when executed by the processor 560, cause the processor 560 to perform the operations described herein with reference to the probe 110 and/or the host 130 (FIG. 1). Instructions 566 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 568 can include any electronic circuitry and/or logic circuitry to facilitate direct or indirect communication of data between the processor circuit 510, the probe 110, and/or the display 132 and/or display 132. In that regard, the communication module 568 can be an input/output (I/O) device. In some instances, the communication module 568 facilitates direct or indirect communication between various elements of the processor circuit 510 and/or the probe 110 (FIG. 1) and/or the host 130 (FIG. 1).

Figure 6:
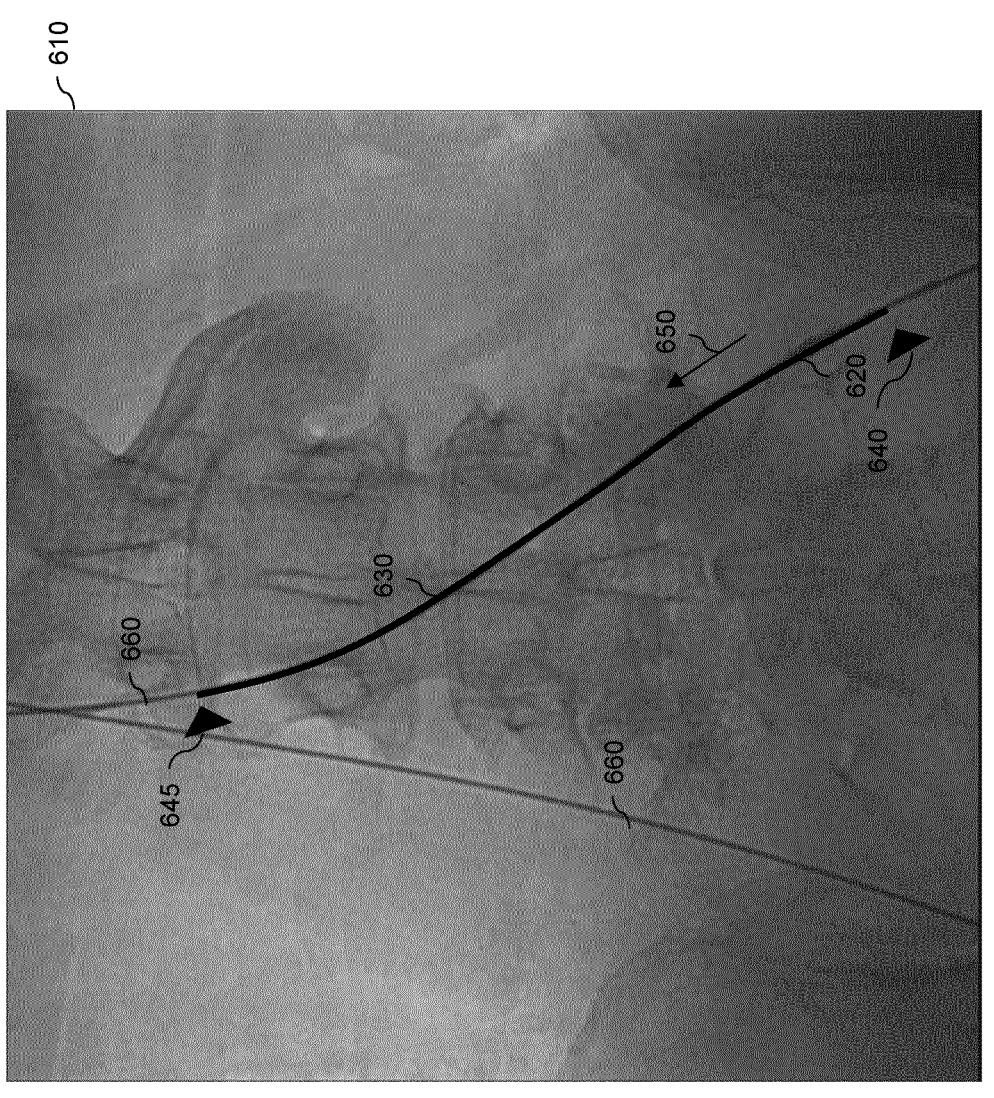
FIG. 6 is a diagrammatic view of an x-ray fluoroscopy image illustrating a pullback procedure, according to aspects of the present disclosure.

FIG. 6 is a diagrammatic view of an x-ray fluoroscopy image illustrating a pullback procedure, according to aspects of the present disclosure. FIG. 6 depicts an x-ray fluoroscopy image 610 showing an intravascular device 620 and guidewires 660. FIG. 6 additionally depicts an intravascular device path 630, a starting indicator 640, an ending indicator 645, and a directional arrow 650.

During a pullback procedure, one or more guidewires 660 may be positioned within one or more lumens of a patient. Because the guidewire 660 may be constructed of a flexible material, the shape of the guidewire 660 may conform to the shape of the lumen in which the guidewire 660 is positioned. The guidewire 660 may include a flexible elongate member. An intravascular device 620 may be positioned within the lumen and travel through the lumen along a guidewire 660, which is positioned within a guidewire lumen of the intra-vascular device 620. The intravascular device 620 can be a catheter or a guide catheter. The intravascular device 620 may be an IVUS catheter. The device 620 may be con-structed of a flexible material, such that the shape of the device 620 may match the curvature of the lumen in which the device 620 is positioned. The intravascular device 620 may include a flexible elongate member. In the fluoroscopy image 610, a radiopaque portion of the intravascular device 620 is visible. The intravascular device 620 may be sub-stantially similar to the device 102 of the intraluminal ultrasound imaging system 101. A user of the system 100 may position the intravascular device 620 at a starting location shown by the indicator 640. With the intravascular device 620 placed at the starting location, the user may begin acquiring fluoroscopy images with the x-ray imaging system 151. The image 610 may be one of the many x-ray fluoros-copy images obtained during the pullback. In some embodi-ments, the fluoroscopy image 610 is an x-ray image obtained while no contrast agent is present within the patient anatomy. In such an embodiment, the lumens (e.g., blood vessel) of the patient may be identified primarily by the positioning of the guidewires 660 within the lumens. In other embodiments, the image 610 may be an x-ray image obtained while a contrast agent is present within the patient anatomy. The contrast agent may make vessel lumens visible within the image 610.

One or a plurality of radiopaque portions of the guidewire 660 are visible in the x-ray image(s) 610 obtained without contrast. The radiopaque portions can be one length or a plurality of lengths of the guidewire 660. In some embodiments, the radiopaque portions of the guidewire 660 are one or a plurality of radiopaque markers. The radiopaque markers can be made of a different material that is more radiopaque than the material used to form other parts of the guidewire 660. In some embodiments, all or substantially all of the guidewire 660 can be radiopaque. In some embodiments, all or substantially all of the portion of the guidewire 660 within the patient body can be radiopaque. In some embodiments, all or substantially all of the distal portion of the guidewire 660 (e.g., the portion of the guidewire being imaged by x-ray) can be radiopaque. For example, the guidewire 660 can be sufficiently thick (e.g., a sufficiently large diameter) to provide radiopacity in x-ray images 610. Such embodiments can include clinical applications in the peripheral venous system, which can involve guidewires with a diameter between 0.014" and 0.038", including values such as 0.014", 0.018", 0.035", 0.038", and/or other values both larger and smaller.

While the x-ray imaging system 151 acquires fluoroscopy images, the user of the system 100 may then begin to move device 620 through the patient lumen along the guidewire 660. The user may pull the device in a direction shown by the arrow 650. As the device 620 moves along the guidewire 660 through the lumen, the device 620 shown in newly acquired fluoroscopy images is shown to move in the direction shown by the arrow 650. The user may continue to pull the device 620 along the guidewire 660 until an ending position 645. The path taken by the device 620 during the pullback procedure may be illustrated by the path 630 within FIG. 6.

As the device 620 moves from the starting position shown by the indicator 640 to the ending position shown by the indicator 645, it may acquire any suitable intravascular data, such as IVUS images. After the device 620 has moved to the ending position, the user may stop acquiring fluoroscopy images with the x-ray imaging system 151 and may remove the device 620 from the lumen. Because the intravascular data was obtained with the device 620 while fluoroscopy images were simultaneously acquired, the intravascular data may be coregistered to the places along the path 630 at which each datum was collected and displayed in relation to that location along the path 630 and/or a representative fluoroscopy image as will be described with greater detail with reference to FIG. 7.

In some embodiments, the intravascular device 620 may be moved in an opposite direction. For example, the device may be moved from the position of indicator 645 to the position of indicator 640. In other words, the device 620 may move from a distal region to a proximal region (e.g., a pullback) or may move from a proximal region to a distal region (e.g., push forward) during the imaging procedure.

It is noted, that the starting and ending positions may represent target locations during an IVUS imaging procedure. Any indicators, such as indicators 640 and/or 645, identifying these locations may not be visible within an x-ray image displayed to a user during a pullback procedure. For example, during an imaging procedure, the system may identify the starting location of the device 620 on the display, but the ending location of the device 620 is not known because the procedure is still in the process of being completed. However, after an IVUS imaging procedure or pullback procedure is completed, during a review phase of the process, indicators 640 and/or 645 identifying both the starting location and the ending location may be displayed to a user of the system.

Figure 7:
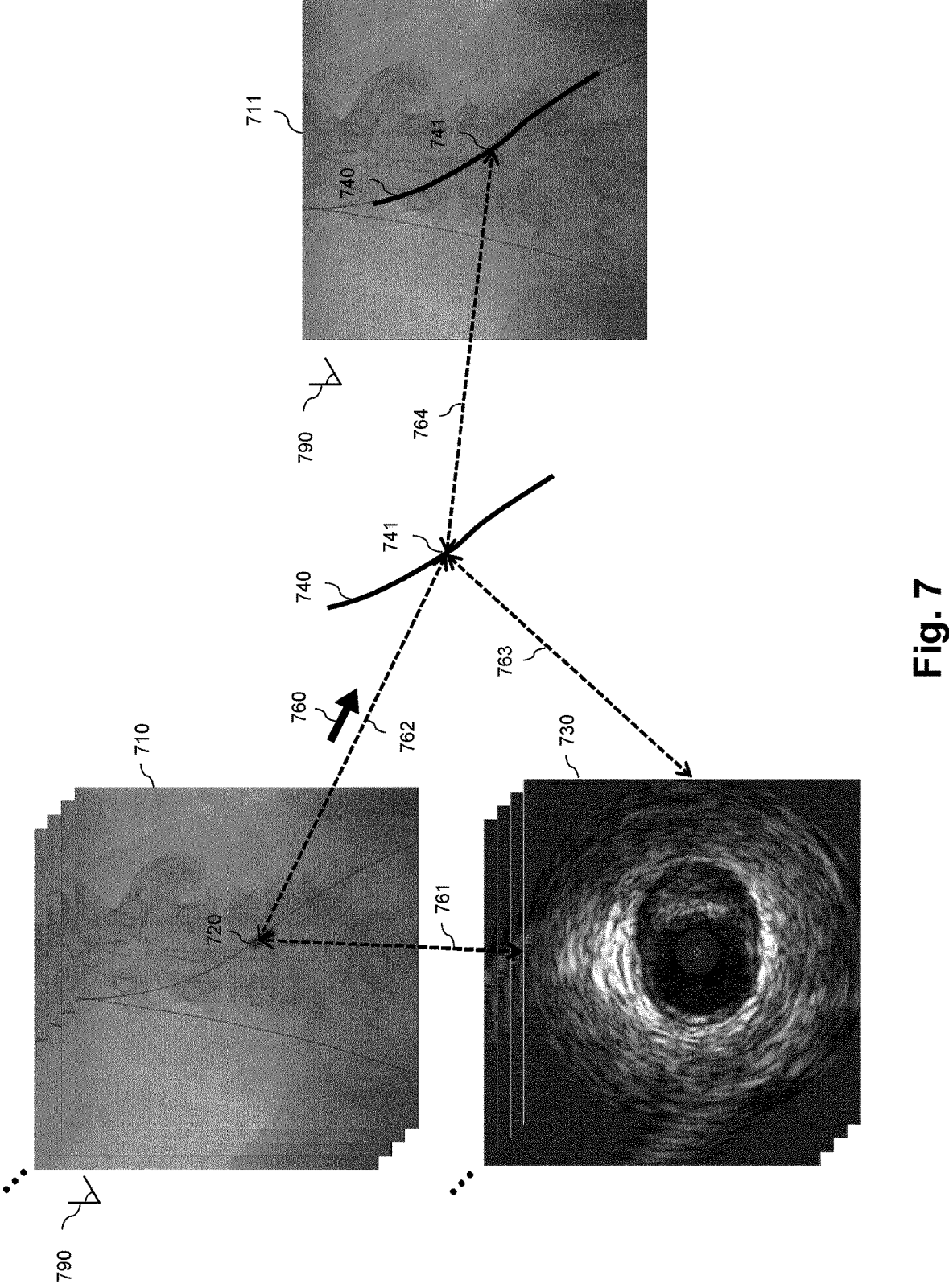
FIG. 7 is a diagrammatic view of a relationship between x-ray fluoroscopy images, intravascular data, and a path defined by the motion of an intravascular device, according to aspects of the present disclosure.

FIG. 7 is a diagrammatic view of a relationship between x-ray fluoroscopy images 710, intravascular data 730, and a path 740 defined by the motion of an intravascular device, according to aspects of the present disclosure. FIG. 7 describes a method of coregistering intravascular data 730 including intravascular images with corresponding locations on one or more fluoroscopy images 710 of the same region of a patient's anatomy.

The patient anatomy may be imaged with an x-ray device while a physician performs a pullback with an intravascular device 720, e.g., while the intravascular device 720 moves through a blood vessel of the anatomy. The intravascular device may be substantially similar to the intravascular device 102 described with reference to FIG. 1. The x-ray device used to obtain the fluoroscopy images 710 may be substantially similar to the x-ray device 152 of FIG. 1. In some embodiments, the fluoroscopy images 710 may be obtained while no contrast agent is present within the patient vasculature. Such an embodiment is shown by the fluoroscopy images 710 in FIG. 7. The radiopaque portion of the intravascular device 720 is visible within the fluoroscopy image 710. The fluoroscopy images 710 may correspond to a continuous image stream of fluoroscopy images and may be obtained as the patient anatomy is exposed to a reduced dose of x-radiation. It is noted that the fluoroscopy images 710 may be acquired with the x-ray source 160 and the x-ray detector 170 positioned at any suitable angle in relation to the patient anatomy. This angle is shown by angle 790.

The intravascular device 720 may be any suitable intravascular device. As the intravascular device 720 moves through the patient vasculature, the x-ray imaging system may acquire multiple fluoroscopy images 710 showing the radiopaque portion of the intravascular device 720. In this way, each fluoroscopy image 710 shown in FIG. 7 may depict the intravascular device 720 positioned at a different location such that a processor circuit may track the position of the intravascular device 720 over time.

As the intravascular device 720 is pulled through the patient vasculature, it may acquire intravascular data 730. In an example, the intravascular data 730 shown in FIG. 7 may be IVUS images. However, the intravascular data may be any suitable data, including IVUS images, FFR data, iFR data, OCT images, intravascular photoacoustic (IVPA) images, or any other measurements or metrics relating to blood pressure, blood flow, lumen structure, or other physiological data acquired during a pullback of an intravascular device.

As the physician pulls the intravascular device 720 through the patient vasculature, each intravascular data point 730 acquired by the intravascular device 720 may be associated with a position within the patient anatomy in the fluoroscopy images 710, as indicated by the arrow 761. For example, the first IVUS image 730 shown in FIG. 7 may be associated with the first fluoroscopy image 710. The first IVUS image 730 may be an image acquired by the intravascular device 720 at a position within the vasculature, as depicted in the first fluoroscopy image 710 as shown by the intravascular device 720 within the image 710. Similarly, an additional IVUS image 730 may be associated with an additional fluoroscopy image 710 showing the intravascular device 720 at a new location within the image 710, and so on. The processor circuit may determine the locations of the intravascular device 720 within each acquired x-ray image 710 by any suitable method. For example, the processor circuit may perform various image processing techniques, such as edge identification of the radiopaque marker, pixel-by-pixel analysis to determine transition between light pixels and dark pixels, filtering, or any other suitable techniques to determine the location of the imaging device 720. In some embodiments, the processor circuit may use various artificial intelligence methods including deep learning techniques such as neural networks or any other suitable techniques to identify the locations of the imaging device 720 within the x-ray images 710.

Any suitable number of IVUS images or other intravascular data points 730 may be acquired during an intravascular device pullback and any suitable number of fluoroscopy images 710 may be obtained. In some embodiments, there may be a one-to-one ratio of fluoroscopy images 710 and intravascular data 730. In other embodiments, there may be differing numbers of fluoroscopy images 710 and/or intravascular data 730. The process of co-registering the intravascular data 730 with one or more x-ray images may include some features similar to those described in U.S. Pat. No. 7,930,014, titled, "VASCULAR IMAGE CO-REGISTRATION," and filed Jan. 11, 2006, which is hereby incorporated by reference in its entirety. The co-registration process may also include some features similar to those described in U.S. Pat. Nos. 8,290,228, 8,463,007, 8,670,603, 8,693,756, 8,781,193, 8,855,744, and 10,076,301, all of which are also hereby incorporated by reference in their entirety.

The system 100 may additionally generate a fluoroscopy-based 2D pathway 740 defined by the positions of the intravascular device 720 within the x-ray fluoroscopy images 710. The different positions of the intravascular device 720 during pullback, as shown in the fluoroscopy images 710, may define a two-dimensional pathway 740, as shown by the arrow 760. The fluoroscopy-based 2D pathway 740 reflects the path of one or more radiopaque portions of the intravascular device 720 as it moved through the patient vasculature as observed from the angle 790 by the x-ray imaging device 152. The fluoroscopy-based 2D pathway 740 defines the path as measured by the x-ray device which acquired the fluoroscopy images 710, and therefore shows the path from the same angle 790 at which the fluoroscopy images were acquired. Stated differently, the 2D pathway 740 describes the projection of the 3D path followed by the device onto the imaging plane at the imaging angle 790. In some embodiments, the pathway 740 may be determined by an average of the detected locations of the intravascular device 720 in the fluoroscopy images 710. For example, the pathway 740 may not coincide exactly with the guidewire in any fluoroscopy image 710 selected for presentation.

As shown by the arrow 762, because the two-dimensional path 740 is generated based on the fluoroscopy images 710, each position along the two-dimensional path 740 may be associated with one or more fluoroscopy images 710. As an example, at a location 741 along the path 740, the first fluoroscopy image 710 may depict the intravascular device 720 at that same position 741. In addition, because a correspondence was also established between the fluoroscopy images 710 and the intravascular data 730 as shown by the arrow 761, intravascular data 730, such as the first IVUS image shown, may also be associated with the location 741 along the path 740 as shown by the arrow 763.

Finally, the path 740 generated based on the locations of the intravascular device 720 within the fluoroscopy images 710 may be overlaid onto any suitable fluoroscopy image 711 (e.g., one of the fluoroscopic images 710 in the fluoroscopic image stream). In this way, any location along the path 740 displayed on the fluoroscopy image 711 may be associated with IVUS data such as an IVUS image 730, as shown by the arrow 764. For example, IVUS image 730 shown in FIG. 7 may be acquired simultaneously with the fluoroscopy image 710 shown and the two may be associated with each other as shown by the arrow 761. The fluoroscopy image 710 may then indicate the location of the intravascular device 720 along the path 740, as shown by the arrow 762, thus associating the IVUS image 730 with the location 741 along the path 740 as shown by the arrow 763. Finally, the IVUS image 730 may be associated with the location within the fluoroscopy image 710 at which it was acquired by overlaying the path 740 with associated data on the fluoroscopy image 711. The pathway 740 itself may or may not be displayed on the image 711.

In the illustrated embodiment of FIG. 7, the co-registered IVUS images are associated with one of the fluoroscopic images obtained without contrast such that that the position at which the IVUS images are obtained is known relative to locations along the guidewire. In other embodiments, the co-registered IVUS images are associated with an x-ray image obtained with contrast (in which the vessel is visible) such that that the position at which the IVUS images are obtained is known relative to locations along the vessel.

Figure 8:
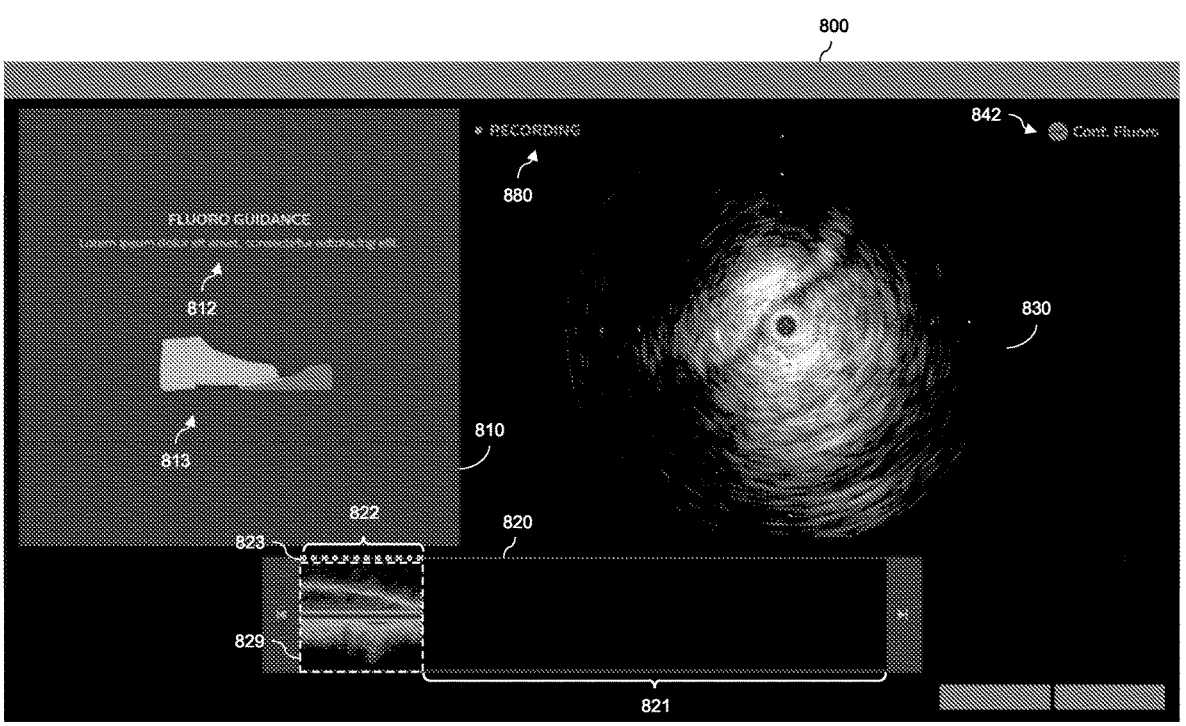
FIG. 8 is a diagrammatic view of a graphical user interface displaying coregistration reliability indicators during a pullback procedure, according to aspects of the present disclosure.

FIG. 8 is a diagrammatic view of a graphical user interface 800 displaying coregistration reliability indicators during a pullback procedure, according to aspects of the present disclosure. The graphical user interface 800 includes an IVUS image 830, an image longitudinal display (ILD) 820 including a region 822, coregistration reliability indicators 823 and 842, a region 810, text 812, a graphical representation 813, and an indicator 880.

The graphical user interface 800 may be displayed to a user of the system 100 via the display 132 (FIG. 1) during an intravascular device pullback procedure. The graphical user interface 800 may display an IVUS image 830. During acquisition, the IVUS image 830 may be a real time or near real time image of the blood vessel in which the IVUS catheter is positioned. Thus, during the pullback procedure, the IVUS image 830 displayed within the graphical user interface 800 may correspond to the most recently acquired IVUS image acquired with the IVUS catheter 620.

The IVUS images acquired with the device 620, may be used to create an ILD 820, shown adjacent to the IVUS image 830. In that regard, IVUS image 830 is a tomographic or radial cross-sectional view of the blood vessel. The ILD 820 provides a longitudinal cross-sectional view of the blood vessel. The ILD 820 can be a stack of the IVUS images acquired at various positions along the vessel, such that the longitudinal view of the ILD 820 is perpendicular to the radial cross-sectional view of the IVUS image 830. In such an embodiment, the ILD 820 may show the length of the vessel, whereas an individual IVUS image 830 is a single radial cross-sectional image at a given location along the length. In another embodiment, the ILD 820 may be a stack of the IVUS images acquired overtime during the imaging procedure and the length of the ILD 820 may represent time or duration of the imaging procedure. The ILD 820 may be generated and displayed in real time or near real time during the pullback procedure. As each additional IVUS image 830 is acquired by the device 620, it may be added to the ILD 820. For example, at a point in time during the pullback procedure, the ILD 820 shown in FIG. 8 may be partially complete. The region 822 of the ILD 820 may correspond to the IVUS images acquired before the point in time during the procedure. The remaining region 821 may be reserved for additional IVUS images to be acquired by the device 620 at future times during the pullback. In some embodiments, the processor circuit may generate an illustration of a longitudinal view of the vessel being imaged based on the received IVUS images. For example, rather than displaying actual vessel image data as the ILD does, the illustration may be a stylized version of the vessel, with e.g., continuous lines showing the lumen border and vessel border.

The graphical user interface 800 may additionally include a number of coregistration reliability indicators, such as the indicators 842, 823, 812, and/or 813.

The coregistration reliability indicator 842 may be a textual guidance element related to the ILD 820 that may indicate to a user, in text, the meaning of visual elements (e.g., indicator 823) that appear in the ILD. The coregistration reliability indicator 842 may convey to the user of the system 100 whether fluoroscopy images are being simultaneously obtained by the x-ray imaging system 151. The indicator 842 may include any suitable symbols, shapes, alphanumeric text, or any other visual element. For example, the indicator may include text adjacent to a symbol as shown in FIG. 8. The text of the indicator 842 may convey to the user that the indicator relates to fluoroscopy images being acquired. For example, as shown, the text may be "Cont. Fluoro," "Continuous Fluoroscopy," "Fluoroscopy Image," or any other suitable term. The symbol of the indicator 842 may additionally convey to the user that it relates to obtaining or not obtaining fluoroscopy images in any suitable manner. For example, if the x-ray imaging system 151 is not acquiring fluoroscopy images, the indicator 842 may alter its appearance to indicate the fact.

The symbol and/or text of the indicator 842 may be a particular color, pattern, or size. For example, if fluoroscopy images are not being acquired by the x-ray imaging system 151, the text and symbol of the indicator 842 may be red and the symbol may be an icon configured to alert the user The text and/or symbol of the indicator 842 may be changed to indicate that fluoroscopy images are or are not being obtained. If fluoroscopy images are being obtained, the indicator 842 may be of a different color than it was to show that fluoroscopy images were not being obtained. For example, if fluoroscopy images are being obtained, the symbol and text of the indicator 842 may be green and the signal may change to a different icon. The indicator 842 may also be animated. For example, the indicator 842 may flash on and off if fluoroscopy images are not being obtained, or animated in any other way. In an exemplary embodiment, the reliability indicator 842 may only be displayed to a user if the x-ray imaging system 151 is not acquiring fluoroscopy images and may not be displayed entirely if fluoroscopy images are being acquired. The indicator 842 may show a current, real time, or near real time operational state of the x-ray imaging system. For example, as the ILD 820 is successively generated during the imaging procedure, the indicator 842 may indicate whether the last IVUS image was obtained by the IVUS imaging catheter while x-ray images were being acquired at the same time or not.

The indicator 823 may include one or more lines similar to the dotted line shown along the upper portion of the region 822 of the ILD 820. The coregistration indicator 823 shown at a top border of the ILD 820, e.g., just above the image content of the ILD 820, may correspond to the status of the coregistration reliability indicator 842 and/or other reliability indicators for the region 822 of the ILD, as will be described hereafter.

The region 822 may correspond to a region within the patient lumen. In the example shown, as the device 620 was moved through the patient lumen, it acquired a number of IVUS images. These IVUS images were used to create the region 822 of the ILD 820. However, as shown by the indicator 823, and the box 829, the IVUS images corresponding to the region 822 were acquired while no fluoroscopy images were obtained. This means, for the example shown in FIG. 8, while the IVUS images corresponding to the region 822 were obtained, the indicator 842 warned the user that no fluoroscopy images were being obtained. Similarly, the coregistration reliability indicator 823 positioned above the region 822 of the ILD 820 also indicates that no fluoroscopy images were obtained while the device 620 moved along the section of the vessel corresponding to the region 822. The indicator 823 may convey this information by its appearance. For example, the indicator 823 may be a line of a particular color and/or pattern. For example, the indicator 823 may convey that no fluoroscopy images were obtained for a particular section because it is a red and dotted or dashed line. The indicator 823 may also be of any other suitable appearance. It may be of any pattern, including but not limited to solid, dashed, dotted, or any other lines. It may also be or include a plurality of symbols, such as multiple shapes or other symbols arranged in a line or according to any other profile.

The indicator 823 may be displayed over the region 822 as shown in FIG. 8 or displayed at any other suitable location. For example, the indicator 823 may be positioned directly beneath the region 822, to either side of the region 822, overlaid over the region 822, or positioned at any other location so as to define the starting and stopping locations of the region 822 along the ILD.

The system 100 may determine whether fluoroscopy images are being obtained by the system 151 by any suitable method. In one embodiment, the intraluminal system 101 and/or the control system 130 may transmit a signal querying the status of the x-ray imaging system 151. The x-ray imaging system 151 may transmit a response signal to the intraluminal imaging system 101 and/or the control system 130 indicating either that it is or is not acquiring fluoroscopy images. The signal may include information concerning whether the system 151 is on, whether the system 151 is in communication with the intraluminal system 101 and/or the system 130, or any other status indicators of the system 151. For example, a status signal from the x-ray imaging system 151 may include three indicators similar to "on, connected, active (acquiring x-ray fluoroscopic images)," if the device is on, connected to the proper systems, including the system 101 and/or the system 130, and acquiring fluoroscopy images. Alternatively, the signal may be "on, connected, inactive," "on, not connected, active" etc. An active status may indicate that the x-ray imaging system 151 is acquiring fluoroscopy images while an inactive status may indicate that the system 151 is not acquiring fluoroscopy images. An inactive status of the x-ray imaging system 151 may be caused by the system 151 not being on, not being in communication with the control system 130 and/or the intraluminal system 101, because the system 151 has not received a signal to begin acquiring fluoroscopy images, or by other hardware or software issues related to the device 152 or the system 151 more generally. An active status of the x-ray imaging system 151 may indicate that the x-ray imaging system 151 and device 152 is on, connected to intraluminal imaging system 101 and/the control system 130, and acquiring fluoroscopic image frames.

In some embodiments, the intraluminal system 101 and/or control system 130 need not query. The x-ray imaging system 151 may transmit a periodic signal (e.g., every 5 seconds, 10 seconds, 30 seconds, 1 minute, etc.) to the intraluminal system 101 and/or control system 130 concerning its status. In other embodiments, the status signal need not originate from the x-ray imaging system 151. For example, if the x-ray imaging system 151 or device 152 is not on or not connected, it may fail to respond to a query or fail to transmit a signal. In this case, an extraluminal system status signal may be generated by the intraluminal system 101 and/or control system 130 and to convey that either no communication is established with the x-ray imaging system 151, the x-ray imaging system 151 or device 152 is not on, or the x-ray imaging system 151 or device 152 is not connected. In these circumstances, coregistration would not be possible.

In some embodiments, any region of the ILD 820 corresponding to sections of the lumen that were imaged without corresponding fluoroscopy images may be additionally or alternatively shaded by a box 829. The box 829 is positioned over the ILD 820. The box 829 may be semi-transparent or patterned in such a way to still allow visibility of the content of the ILD along the region 822 but clearly indicate to the user that images of the region 822 were acquired without corresponding fluoroscopy images. In some embodiments, the box 829 may be of a similar color to the indicator 842 and/or the indicator 823 or may differ.

FIG. 8 additionally depicts a region 810 and corresponding text 812 and graphic 813. The region 810 may be reserved for displaying fluoroscopy images within the graphical user interface 800. In the example shown in FIG. 8, a fluoroscopy image may not have been simultaneously obtained with the acquired IVUS image 830. Therefore, the region 810 may not display a fluoroscopy image. As described previously, the indicator 842 may also indicate that no fluoroscopy images are obtained. Text 812 may similarly indicate to the user of the system 100 that fluoroscopy images are not being obtained, may contain instructions on how or when to acquire fluoroscopy images, or provide any other suitable information to the user. The graphic 813 may also indicate to the user that fluoroscopy images are not being obtained, provide guidance on how or when to acquire fluoroscopy images, and may be of any suitable appearance, including various shapes, depictions, or patterns.

In some embodiments, the graphical user interface 800 may also include an indicator 880. After a user of the system 100 has positioned the intravascular device 620 within the patient lumen at the desired location and completed any other necessary procedural preparation steps, including, for example, engaging the x-ray imaging system 151 to acquire fluoroscopy images, the user may direct the intraluminal imaging system 101 to being acquiring images. Once the intraluminal system 101 begins to acquire IVUS images, it may do so continuously, but not store the images. The user may then direct the system 101 to being to store acquired IVUS images by any action, for example, by pressing a record button. The system 100 may then begin to store the IVUS images acquired. The recording indicator 880 may indicate to the user that the system 100 is storing IVUS images. After the system 101 begins storing IVUS images, the ILD 820 may also begin to be constructed.

Figure 9:
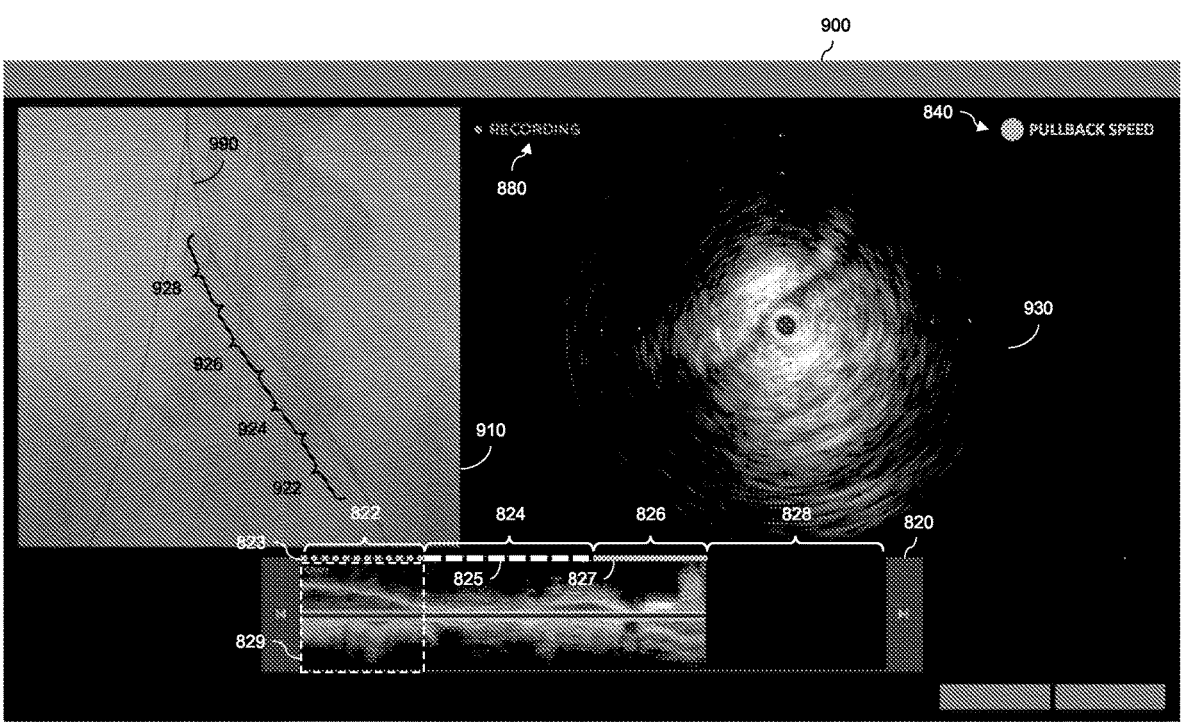
FIG. 9 is a diagrammatic view of a graphical user interface displaying coregistration reliability indicators during a pullback procedure, according to aspects of the present disclosure.

FIG. 9 is a diagrammatic view of a graphical user interface 900 displaying coregistration reliability indicators during a pullback procedure, according to aspects of the present disclosure. The graphical user interface 900 may be substantially similar to the graphical user interface 800. The graphical user interface 900 may display to the user a coregistration reliability indicator 840. The graphical user interface 900 also displays to the user an IVUS image 930, the ILD 820 including the region 822, indicator 823, and box 829, as well as a region 824 and indicator 825, a region 826 and indicator 827, and a region 828. The interface 900 additionally displays a fluoroscopy image 910 showing regions 922, 924, 926, and 928.

The graphical user interface 900 may correspond to a display presented to the user of the system 100 during a pullback procedure. The fluoroscopy image 910 may be one image of a multiple images received by the x-ray imaging system 151 during a pullback procedure. For example, the fluoroscopy image 910 may be one frame in a continuous or nearly continuous stream of x-ray images received by the x-ray imaging system 151. In some embodiments, the fluoroscopy image 910 may only be displayed to a user of the system when if the x-ray imaging system 151 is currently obtaining x-ray images as shown by the indicator 842 and discussed with reference to FIG. 8.

The IVUS image 930 shown in the interface 900 may be any suitable IVUS image acquired by the device 620 as it moved along the guidewire from marker 980 to marker 985. The IVUS image 930 may be similar to the IVUS image 830 in that it represents an ultrasound image generated by the intravascular device 620.

The coregistration indicator 840 shown in the graphical user interface 900 may indicate to the user of the system whether the intravascular device 620 is being moved at an appropriate speed. To obtain high quality intravascular data and correctly coregister acquired intravascular data with associated x-ray images, the intravascular device 620 must be moved through the lumen of a patient at an appropriate rate of speed. If the device is moved through the lumen too quickly, it may lead to either poor quality intravascular data or improper coregistration. The system 100 may determine the speed at which a device 620 moves through a patient lumen by unit tracking the intravascular device 620 in obtained fluoroscopy images. The system 100 may then compare the measured speed of the device 620 to a target speed previously determined by the user or based on suggested speeds provided by the manufacturer of the device 620 or system 100 or based on any other suitable parameters. In that regard, aspects of the present disclosure can include features similar to those described in U.S. Publication No. 2020/0069264, titled "Intravascular Device Movement Speed Guidance and Associated Devices, Systems, And Methods," which is incorporated by reference herein in its entirety. Aspects of the present disclosure may also include features similar to those described in U.S. Publication No. 2020/0129143, titled "Speed Determination for Intraluminal Ultrasound Imaging and Associated Devices, Systems, and Methods," which is also incorporated by reference herein in its entirety.

In the example shown in FIG. 9, the ILD 820 shows the same region 822 previously discussed with reference to FIG. 8. Additionally, as the pullback procedure progresses, the other regions of the ILD 820 may be populated to include additional regions, including, for example, the region 824 and the region 826. The region 828 may correspond to a section of the vessel that has not been imaged yet but may be later during the procedure. Just as the region 822 corresponded to the status of the coregistration reliability indicator 842 of FIG. 8, any of the regions 824, 826, or 828 may correspond to a different status of the coregistration indicator 842 or the coregistration indicator 840.

The coregistration indicator 840, like the coregistration indicator 842, may include any suitable symbols, shapes, alphanumeric text, or any other visual element. For example, the indicator may include text adjacent to a symbol as shown in FIG. 9. The text of the indicator 840 may convey to the user that the indicator relates to the pullback speed of the device 620. For example, as shown, the text may be "Pullback Speed," "Speed," "Rate," or any other suitable term. The symbol of the indicator 840 may additionally convey to the user that it relates to the pullback speed in any suitable manner. If the device is being moved too quickly through the lumen, the indicator 840 may alter its appearance to indicate the fact. The symbol and/or text of the indicator 840 may be a particular color, pattern, or size. In one example, the text and/or symbol of the indicator 840 may be of a red color if the pullback speed is too high. The symbol may also be configured to indicate that the speed is too fast. In some embodiments, the text may also be changed to indicate that the speed is too fast. Like the indicator 842, the indicator 840 may additionally or alternatively be animated. For example, the symbol may flash on and off repeatedly to indicate the speed being too fast or may be animated in any other way. If the pullback speed of the device 620 is appropriate, the indicator 840 may be altered to show that as well. For example, the indicator 840 may be of a different color, such as green, to show an appropriate speed. Similarly, the indicator 840 may be of any color, pattern, size, or may be animated in any way to show that the device 620 is moving at an appropriate rate of speed. In an exemplary embodiment, the reliability indicator 840 may only be displayed to a user if the pullback speed is too fast and may not be displayed entirely if the pullback speed is within a predetermined range of the target pullback speed. This range may be indicated by a high threshold speed and low threshold speed, or a target speed with an acceptable range above and below this target speed. The target speed may vary depending on the clinical and imaging scenarios. In one example, such as for peripheral venous procedures, the target speed of the device may be 15 mm/s. When the system 100 detects that the device 620 is moving at a speed greater than this target, the reliability indicator 840 may be displayed. The target speed may also be determined by or converted to units such as pixels per second within a fluoroscopy image.

In some embodiments, the indicator 840 may additionally indicate if the pullback speed of the device 620 is too slow and may do so by being of any suitable appearance, as has been described.

Each region of the ILD 820 may also correspond to a region along the guidewire 990 shown within the fluoroscopy image 910. For example, the region 822 of the ILD 820 may correspond to the region 922 along the guidewire 990, the region 824 may correspond to the region 924, the region 826 may correspond to the region 926, and the region 828 may correspond to the region 928. It is noted that the regions 922, 924, 926, and 928 may not be identified within the fluoroscopy image 910 but may be.

In the example shown in FIG. 9, and as discussed previously with reference to FIG. 8, the region 822 may indicate that along the imaged vessel within the region 922 of the fluoroscopy image 910, the x-ray imaging system 151 was not acquiring fluoroscopy images. This may be indicated by the indicator 823 and/or the box 829. In some embodiments, for regions like region 822 along which no fluoroscopy images are obtained, the indicator 823 and/or box 829 may additionally convey information relating to the pullback speed of the catheter along the region. For example, if no fluoroscopy images were obtained for a region and the pullback speed of the catheter was appropriate, the indicator 823 and/or box 829 may indicate these statuses. The appearance of the indicator 823 and/or box 829 may be altered in any of the ways previously described to show these two criteria. Conversely, if the device 620 was moved too quickly through the region for which no fluoroscopy images were obtained, the appearance of the indicator 823 and/or the box 829 may again be altered to show these two criteria.

Similarly, the region 824 shown adjacent to the region 822 may indicate that along the imaged vessel with the region 924, the x-ray imaging system 151 was acquiring fluoroscopy images and the pullback speed was appropriate. This would indicate that as the device 620 passed along the guidewire from the region 922 to the 924 within the vessel, the x-ray imaging system 151 began acquiring fluoroscopy images. At that point in time, the indicator 842 would have either disappeared, or otherwise changed to indicate that fluoroscopy images were being acquired. At the location between 922 and 924, the user of the system 100 also slowed the speed of the device 620 to within the target range causing the indicator 840 to also either disappear or otherwise change to indicate that the device 620 was moving at an appropriate speed. The indicator 825 may, therefore, indicate that throughout region 824/region 924, fluoroscopy images were being obtained and the pullback speed of the device 620 was appropriate.

The region 826 shown adjacent to the region 824 may indicate that along the imaged vessel with the region 926, the x-ray imaging system 151 was acquiring fluoroscopy images but the pullback speed was too fast. This would indicate that as the device 620 passed along the guidewire from the region 924 to the 926 within the vessel, the user of the system 100 increased the speed of the device 620 to exceed the target range causing the indicator 840 to either appear or otherwise change to indicate that the device 620 was moving too quickly. The indicator 827 may correspond to those two parameters, namely that throughout the region 826/region 926, fluoroscopy images were being obtained but the pullback speed of the device 620 was too high.

Finally, the region 828 shown adjacent to the region 826 may be reserved for the stretch of the vessel shown by 928 on the fluoroscopy image 910 and may therefore be populated as the region 928 is imaged by the device 620. If the region 928 was imaged while both fluoroscopy images being obtained and with the device 620 moving at an appropriate rate of speed, a similar line to indicator 825 would appear above the ILD along region 828. The new line would be of an identical color, pattern, width, etc. to the indicator 825 showing the same two parameters, e.g. that fluoroscopy images were obtained and the device 620 moved at an appropriate speed. This would indicate to the user that along the regions 824 and 828 or along the regions 924 and 928, the IVUS data acquired and coregistration of the data with the fluoroscopy images were ideal and does not need to be imaged again. However, if the region 828/region 928 was not imaged with the device 620 moving at an appropriate rate of speed but with fluoroscopy images being acquired simultaneously, the line would be similar to the indicator 827. In this way, the indicators 823, 825, and 827 and similar indicators positioned along the ILD corresponding to the status of the indicators 840 and 842 throughout a pullback procedure provide the user with a summary of the success or reliability of the pullback procedure. These reliability indicators allow the user to decide whether to image again certain regions of the vessel and indicates which regions would most likely need to be imaged again. This makes the pullback procedure more efficient and reliable.

It is noted that any of the coregistration reliability indicators discussed herein, including the indicators 842, 840, 823, 825, 827, and 829 may be stored by the system 100 in a memory. These indicators may be stored in conjunction with the IVUS images 930, x-ray images 910, and ILD 820. The locations of these indicators, with respect to the ILD 820, x-ray images 910, and/or IVUS images 930 and/or the graphical user interface 900 generally may also be stored. In this way, a user of the system 100 or any other individual may view all of the information and/or data discussed with reference to FIG. 8 and FIG. 9, which are obtained and displayed during the initial imaging procedure, at any time after the procedure (e.g., during review of the IVUS images, such as after co-registration).

FIG. 10 is a flow diagram for a method 1000 for coregistration, according to aspects of the present disclosure. As illustrated, the method 1000 includes a number of enumerated steps, but embodiments of the method 1000 may include additional steps before, after, or in between the enumerated steps. In some embodiments, one or more of the enumerated steps may be omitted, performed in a different order, or performed concurrently. The steps of the method 1000 can be carried out by any suitable component within the system 100 and all steps need not be carried out by the same component. In some embodiments, one or more steps of the methods 1000 can be performed by, or at the direction of, a processor circuit of the system 100 (e.g., the processor circuit 510 of FIG. 5), including, e.g., the processor 560 or any other component.

At step 1010, the method 1000 includes receiving a plurality of intraluminal images obtained by the intraluminal imaging catheter or guidewire during movement of the intraluminal imaging catheter or guidewire within a body lumen of a patient. For example, step 1010 can include receiving a plurality of IVUS images obtained by the IVUS catheter during a pullback of the IVUS catheter within a blood vessel of a patient.

At step 1020, the method 1000 includes receiving a signal representative of a status of the extraluminal imaging device during the movement of the intraluminal imaging catheter or guidewire. For example, step 1020 can include receive a signal representative of a status of the x-ray imaging device during the pullback of the IVUS catheter. The status can include an active status in which the x-ray imaging device is obtaining x-ray fluoroscopic images of the pullback or an inactive status in which the x-ray imaging device is not obtaining x-ray fluoroscopic images of the pullback.

At step 1030, the method 1000 includes determining a speed of the movement of the intraluminal imaging catheter or guidewire. For example, step 1030 can include determining a speed of the movement of the IVUS catheter.

At step 1040, the method 1000 includes generating screen display including first graphical representation based on plurality of intraluminal images and second graphical representation based on status of extraluminal imaging device and/or the speed. The first graphical representation and the second graphical representation can be positioned proximate to one another. For example, step 1040 can include generating a screen display including a longitudinal view of the blood vessel based on the plurality of IVUS images and one or more color-coded graphical representations based on the status of the x-ray imaging device and/or the speed. The one or more graphical representations can be positioned over or adjacent to the longitudinal view. The one or more color-coded graphical representations include an indication that the plurality of IVUS images cannot be co-registered to an x-ray image, an indication that the plurality of IVUS images can be co-registered to the x-ray image, and/or an indication of possible error, lower/decreased reliability, and/or lower/decreased accuracy in co-registration of the plurality of IVUS images to the x-ray image.

At step 1050, the method 1000 includes outputting the screen display to a display in communication with the processor circuit.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:
a processor circuit configured for communication with an extraluminal imaging device and an intraluminal imaging catheter or guidewire, wherein the processor circuit is configured to:
receive a plurality of intraluminal images obtained by the intraluminal imaging catheter or guidewire during movement of the intraluminal imaging catheter or guidewire within a body lumen of a patient;
receive a signal representative of a status of the extraluminal imaging device during the movement of the intraluminal imaging catheter or guidewire;
generate a screen display comprising:
a first graphical representation based on the plurality of intraluminal images; and
a second graphical representation based on the status of the extraluminal imaging device and a speed of the movement of the intraluminal imaging catheter or guidewire, wherein the first graphical representation and the second graphical representation are positioned proximate to one another; and
output the screen display to a display in communication with the processor circuit,
wherein the second graphical representation is configured to indicate that the plurality of intraluminal images can be co-registered to an extraluminal image in response to:
the status of extraluminal imaging device comprising an active status; and
the speed satisfying a threshold.

2. The system of claim 1, wherein the second graphical representation is configured to indicate that the plurality of intraluminal images cannot be co-registered to the extraluminal image in response to the status of extraluminal imaging device comprising an inactive status.

3. The system of claim 1, wherein the first graphical representation comprises a longitudinal view of the body lumen.

4. The system of claim 3, wherein the longitudinal view of the body lumen comprises a stack of the plurality of intraluminal images.

5. The system of claim 3, wherein the second graphical representation is positioned at a border of the longitudinal view.

6. The system of claim 5, wherein the second graphical representation comprises a plurality of symbols positioned along the border.

7. The system of claim 3, wherein the second graphical representation comprises an overlay on the longitudinal view.

8. The system of claim 1, wherein a length of the second graphical representation is representative of at least one of a distance or a time during the movement of the intraluminal imaging catheter or guidewire that corresponds to the status of the extraluminal imaging device.

9. The system of claim 7, wherein the second graphical representation comprises the overlay in response to the status of the extraluminal imaging device comprising an inactive status.

10. The system of claim 1, wherein the processor circuit is configured to determine the speed.

11. The system of claim 1, wherein the second graphical representation is configured to indicate decreased reliability in co-registration of the plurality of intraluminal images to the extraluminal image in response to:

the status of extraluminal imaging device comprising an active status; and the speed not satisfying a threshold.

12. The system of claim 1, wherein the second graphical representation is color-coded based on at least one of the status of the extraluminal imaging device or the speed.

13. The system of claim 1, wherein the second graphical representation comprises text.

14. The system of claim 1, wherein the screen display comprises a plurality of second graphical representations.

15. A system, comprising:

an intravascular ultrasound (IVUS) or optical coherence tomography (OCT) catheter; and a processor circuit configured for communication with an x-ray imaging device and the IVUS or OCT catheter, wherein the processor circuit is configured to:

receive a plurality of IVUS or OCT images obtained by the IVUS or OCT catheter during a pullback of the IVUS or OCT catheter within a blood vessel of a patient;

receive a signal representative of a status of the x-ray imaging device during the pullback of the IVUS or OCT catheter, wherein the status comprises one of:

an active status in which the x-ray imaging device is obtaining x-ray fluoroscopic images of the pullback; or an inactive status in which the x-ray imaging device is not obtaining x-ray fluoroscopic images of the pullback;

determine a speed of the movement of the IVUS or OCT catheter;

generate a screen display comprising:

a longitudinal view of the blood vessel based on the plurality of IVUS or OCT images; and one or more color-coded graphical representations based on at least one of the status of the x-ray imaging device or the speed, wherein the one or more graphical representations are positioned over or adjacent to the longitudinal view, and wherein the one or more color-coded graphical representations comprise at least one of:

an indication that the plurality of IVUS or OCT images cannot be co-registered to an x-ray image;

an indication that the plurality of IVUS or OCT images can be co-registered to the x-ray image; or an indication of decreased reliability in co-registration of the plurality of IVUS or OCT images to the x-ray image; and output the screen display to a display in communication with the processor circuit.

16. The system of claim 1, further comprising the intraluminal imaging catheter or guidewire.

17. The system of claim 16, wherein the intraluminal imaging catheter or guidewire comprises an intravascular imaging catheter configured for intravascular ultrasound (IVUS) or optical coherence tomography (OCT), wherein the plurality of intraluminal images comprises a plurality of IVUS images or a plurality of OCT images.

18. A system, comprising:

a processor circuit configured for communication with an extraluminal imaging device and an intravascular catheter or guidewire, wherein the processor circuit is configured to:

receive a plurality of intravascular data points obtained by the intravascular catheter or guidewire during movement of the intravascular catheter or guidewire within a blood vessel of a patient;

receive a signal representative of a status of the extraluminal imaging device during the movement of the intravascular catheter or guidewire;

generate a screen display comprising:

a first graphical representation based on the plurality of intravascular data points; and a second graphical representation based on the status of the extraluminal imaging device and a speed of the movement of the intravascular catheter or guidewire, wherein the first graphical representation and the second graphical representation are positioned proximate to one another; and output the screen display to a display in communication with the processor circuit, wherein the second graphical representation is configured to indicate that the plurality of intravascular data points can be co-registered to an extraluminal image in response to:

the status of extraluminal imaging device comprising an active status; and the speed satisfying a threshold.

19. The system of claim 18, further comprising the intravascular catheter or guidewire, wherein the intravascular catheter or guidewire comprises an intravascular pressure-sensing guidewire or an intravascular flow-sensing guidewire such that the plurality of intravascular data points is representative of at least one of intravascular pressure or intravascular flow.

20. The system of claim 19, further comprising the intravascular catheter or guidewire, wherein the intravascular catheter or guidewire comprises an intravascular imaging catheter configured for intravascular ultrasound (IVUS) or optical coherence tomography (OCT) such that the plurality of intravascular data points comprises a plurality of IVUS images or a plurality of OCT images.

* * * * *